(12) United States Patent
O'Neill et al.

(10) Patent No.: US 7,265,163 B2
(45) Date of Patent: *Sep. 4, 2007

(54) LIGHT EMITTING POLYMER

(75) Inventors: Mary O'Neill, Hull (GB); Stephen Malcolm Kelly, Beverly (GB); Adam Edward Alexander Contoret, Bradley Stoke (GB); Gary James Richards, Oxford (GB)

(73) Assignee: University of Hull, Hull (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/859,446

(22) Filed: Jun. 1, 2004

(65) Prior Publication Data

US 2005/0004252 A1    Jan. 6, 2005

Related U.S. Application Data

(63) Continuation of application No. 10/187,381, filed on Jul. 1, 2002, which is a continuation-in-part of application No. 09/898,748, filed on Jul. 3, 2001, now abandoned.

(30) Foreign Application Priority Data

Jun. 29, 2001 (GB) ................................ 0115986.2

(51) Int. Cl.
C08F 2/46 (2006.01)
C09K 19/00 (2006.01)

(52) U.S. Cl. ...................... 522/168; 522/149; 522/162; 522/178; 522/180; 252/299.1; 252/299.62; 252/299.69; 252/299.67; 252/299.01; 428/2.1

(58) Field of Classification Search ................. 522/167, 522/168, 149, 162; 428/2.1; 252/299.1, 252/299.62, 299.69, 299.67, 299.01
See application file for complete search history.

(56) References Cited

U.S. PATENT DOCUMENTS

| | | | |
|---|---|---|---|
| 5,059,863 A | 10/1991 | Tashiro et al. |
| 5,700,393 A | 12/1997 | Kelly |
| 5,707,544 A | 1/1998 | Kelly |
| 5,748,271 A | 5/1998 | Hikmet et al. |
| 5,773,179 A | 6/1998 | Mehl et al. |
| 5,851,424 A | 12/1998 | Kelly |
| 6,201,087 B1 | 3/2001 | Herr et al. |
| 6,218,061 B1 | 4/2001 | Hanna et al. |
| 6,309,901 B1 | 10/2001 | Tahon et al. |
| 6,489,044 B1 | 12/2002 | Chen et al. |
| 2002/0158574 A1 | 10/2002 | Wolk et al. |

FOREIGN PATENT DOCUMENTS

EP    1011154 A1    6/2000

OTHER PUBLICATIONS

Contoret et al. Polarized Electroluminescence from an Anisotropic Nematic Network on a Non-contact Photoalignment Layer. Advanced Materials, No. 13, Jul. 2000, pp. 971-973.*
Jackson et al, "An Investigation of the Role of Cross-Linking and Photodegradation of Side-Chain Coumarin Polymers in the Photoalignment of Liquid Crystals, "Chemical Materials, 2001, vol. 13, pp. 694-703, 2001 American Chemical Society, USA.
Contoret et al, "The Photopolymerization and Cross-Linking of Electroluminescent Liquid Crystals Containing Methacrylate and Diene Photopolymerizable End Groups for Multilayer Organic Light-Emitting Diodes,"Chemical materials, 2002, vol. 14, pp. 1477-1487, 2002 American Chemical Society, USA.
Contoret et al, "Polarized Electroluminescence from an Anisotropic Nematic Network on a Non-Contract Photoalignment Layer,"Advanced Materials, vol. 12, No. 13, Jul. 5, pp. 971-973.
Jackson et al, "Alignment models for coumarin-containing polymers for liquid crystal displays, "Proceedings of SPIE, Liquid Crystal Materials, Devices, and Applications VII, SPIE vol. 3635, Jan. 1999, pp. 38-47, San Jose, California, USA.
Hindmarsh et al, "New Coumarin Polymers as Non-Contact Alignment Layers for Liquid Crystals," Molecular Crystal Liquid Crystal, 1999, vol. 332, pp. 439-446, Gordon and Breach Science Publishers, Malaysia.
Contoret et al, Electroluminescent Nematic Polymer Networks with Polarised Emission, Molecular Crystal and Liquid Crystal, 2001, vol. 364, pp. 511-518, Gordon and Breach Science Publishers, USA.
Contoret et al, "Crosslinked reactive mesogens and photo-chemical alignment for organic polarised EL," Synthetic Metals, 2001, Vo. 121, pp. 1645-1646, 2001 Elsevier Science B.V., UK.
Pei et al, "1,3-4-Oxadiazole-Containing Polymers as Electron-Injection and Blue Electroluminescent Materials in Polymer Light-Emitting Diodes,"Chemical Materials, 1995, vol. 7, pp. 1568-1575, 1995 Americal Chemical Society, USA.
Peregrine Orr Jackson et al, "An Investigation of the Role of Cross-Linking and Photodegradation of Side-Chain Coumarin Polymers in the Photoalignment of Liquid Crystals", Journal 2001 American Chem. Soc. Pub. on Web Jan. 30, 2001, Chem. Matter No. 2 2001, vol. 13, 694-703, USA.
Adam E.A. Contoret et al, "The Photopolymerization and Cross-Linking of Electroluminescent Liquid Crystals Containing Methacrylate and Diene Photopolymerizable End Groups for Multilayer Organic Light-Emitting Diodes", Journal 2001 Americal Chem. Soc. Web. Mar. 20, 2002, Chem. Matter, No. 4, 2002, vol., 14, 1477-1487, USA.

(Continued)

*Primary Examiner*—Sanza L. McClendon
(74) *Attorney, Agent, or Firm*—Martin Fleit; Paul D. Bianco; Fleit Kain Gibbons Gutman Bongini & Bianco P.L.

(57) ABSTRACT

There is provided a process for forming a light emitting polymer comprising photopolymerization of a reactive mesogen having an endgroup which is susceptible to photopolymerization e.g. by a radical polymerization process. Also provided are methods for using the light emitter in displays, backlights, electronic apparatus and security viewers.

30 Claims, 12 Drawing Sheets

OTHER PUBLICATIONS

C. Sanchez et al, Polarized photoluminescence and order parameters of "in situ" photopolymerized liquid films. J. of Applied Physic. vol. 87(1), 2000, 274-279.

Kasim et al. A simple method for fabricating polymeric light emitting diodes. Chem. Mater., 10(1), 235-237, 1998.

Bacher et al. Synthesis and Characterization of conjugated reactive mesogen. J. Mater. Chem., 1999, 9, 2985-2989 (1999).

Sachez et al. Mesomorphic and Orientational Study of Materials Processed by In Situ photopolymerization of Reactive LC. Chem. Mater., 11 (10) 2804-2812, 1999.

* cited by examiner

SCHEME 1

SCHEME 2

SCHEME 3

SCHEME 4

SCHEME 5

SCHEME 6

SCHEME 7

Reagents: (a) (α) K₂CO₃, CH₃COC₂H₅; (b) (i) BuLi, THF (ii) B(OCH₃)₃ (iii) HCl_aq; (c) Br₂, HBr_aq; (d) Pd(Ph₃)₄, Na₂CO₃, H₂O, DME; (e) (i) BBr₃, CHCl₃ (ii) HCl_aq; (f) pyridine, CH₂Cl₂.

SCHEME 8

LIGHT EMITTING POLYMER

This application is a continuation of Ser. No. 10/187,381, which is a continuation-in-part of Ser. No. 09/898,748 filed Jul. 3, 2001 and claims priority from GB Application No. 0115986.2 filed Jun. 29, 2001, which is here incorporated by reference in its entirety.

BACKGROUND OF THE INVENTION

1. Field of the Invention

The present invention relates to polymerisation process for forming light emitting polymers and networks thereof. The light emitting polymer may be used as a source of electroluminescence for use in displays for electronic products.

2. Prior Art

Modern consumer electronics require cheap, high-contrast displays with good power efficiency and low drive voltages. Particular applications include displays for mobile phones and hand-held computers.

Conventional displays comprise twisted nematic liquid crystal displays (TN-LCDs) with active matrix addressing and super-twisted nematic liquid crystal displays (STN-LCDs) with multiplex addressing. These however require intense back lighting which presents a heavy drain on power. The low intrinsic brightness of LCDs is believed to be due to high losses of light caused by the absorbing polarizers and filters which can result in external transmission efficiencies of as low as 4%.

SUMMARY OF THE INVENTION

The Applicants have now devised a new class of light emitting polymers. These can be employed in displays which offer the prospect of lower power consumption and/or higher brightness. The combination of these new light emitting polymers with existing LCD technology offers the possibility of low-cost, bright, portable displays with the benefits of simple manufacturing and enhanced power efficiency.

The light emitting polymer is obtainable by a polymerization process. The process involves the polymerization of reactive mesogens (e.g. in liquid crystal form) via photopolymerization of suitable end-groups of the mesogens.

According to one aspect of the present invention there is provided a process for forming a light emitting polymer comprising photopolymerization of a reactive mesogen having the formula:

B-S-A-S-B         (general formula 1)

wherein

A is a chromophore;

S is a spacer; and

B is an endgroup which is susceptible to photopolymerization.

The polymerisation typically results in a light emitting polymer comprising arrangements of chromophores (e.g. uniaxially aligned) spaced by a crosslinked polymer backbone. A typical process is shown schematically in FIG. 1 from which it may be seen that the polymerisation of reactive monomer 10 results in the formation of crosslinked polymer network 20 comprising crosslink 22, polymer backbone 24 and spacer 26 elements.

Suitable chromophore (A) groups include fluorene, vinylenephenylene, anthracene, perylene and any derivatives thereof. Useful chromophores are described in A. Kraft, A. C. Grimsdale and A. B. Holmes, Angew. Chem. Int. Ed. Eng. [1998], 37, 402.

Suitable spacer (S) groups comprise organic chains, including e.g. flexible aliphatic, amine, ester or ether linkages. The chains may be saturated or unsaturated and be linear or branched. Aliphatic spacers are preferred. The presence of spacer groups aids the solubility and lowers the melting point of the light emitting polymer which assists the spin coating thereof.

Suitable endgroups are susceptible to photopolymerization (e.g. by a radical process using UV radiation, generally unpolarized). Preferably, the polymerization involves cyclopolymerization (i.e. the radical polymerization step results in formation of a cyclic entity).

A typical polymerization process involves exposure of a reactive mesogen of general formula 1 to UV radiation to form an initial radical having the general formula as shown below:

B-S-A-S-B•         (general formula 2)

wherein A, S and B are as defined previously and B• is a radicalised endgroup which is capable of reacting with another B endgroup (particularly to form a cyclic entity). The B• radicalised endgroup suitably comprises a bound radical such that the polymerisation process may be sterically controlled.

Suitable endgroups include dienes such as 1,4, 1,5 and 1,6 dienes. The diene functionalities may be separated by aliphatic linkages, but other inert linkages including ether and amine linkages may also be employed.

Methacrylate endgroups have been found to be less suitable than dienes because the high reactivity of the radicals formed after the photoinitiation step can result in a correspondingly high photodegradation rate. By contrast, it has been found that the photodegradation rate of light emitting polymers formed from dienes is much lower. The use of methacrylate endgroups also does not result in cyclopolymerization.

Where the endgroups are dienes the reaction typically involves cyclopolymerization by a sequential intramolecular and intermolecular propagation: A ring structure is formed first by reaction of the free radical with the second double bond of the diene group. A double ring is obtained by the cyclopolymerization which provides a particularly rigid backbone. The reaction is in general, sterically controlled.

Suitable reactive mesogens have the general formula:

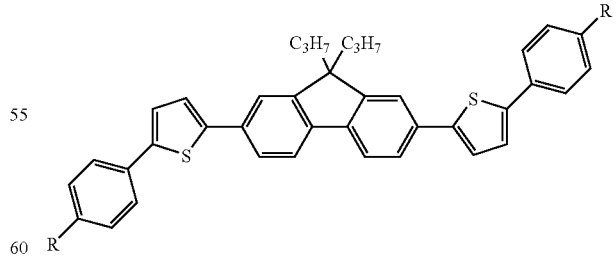

wherein R has the general formula: X—S2-Y-Z and wherein

X=O, $CH_2$ or NH and preferably X=O;

S2=linear or branched alkyl or alkenyl chain optionally including a heteroatom (e.g. O, S or NH) and preferably S2=a linear alkyl chain;

Y=O, CO$_2$ or S and preferably Y=CO$_2$; and

Z=a diene (end-group) and preferably Z=a 1,4, 1,5 or 1,6 diene.

Exemplary reactive mesogens have the general formula:

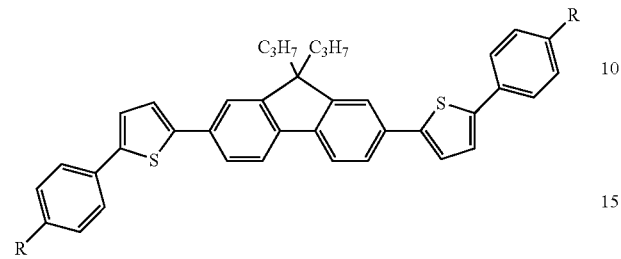

wherein R is:

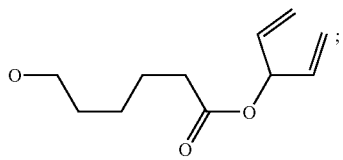
(Compound 3)

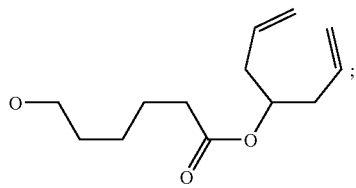
(Compound 4)

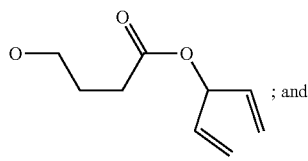
(Compound 5); and

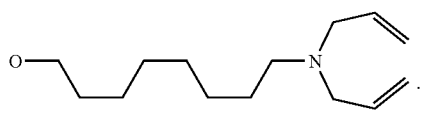
(Compound 6)

An exemplary reactive mesogen has the formula:

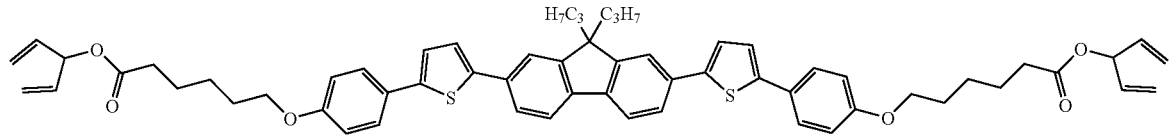

(Compound 3)

All of Compounds 3 to 6 exhibit a nematic phase with a clearing point (N-I) between 79 and 120° C.

Other suitable exemplary reactive mesogens have the general formula:

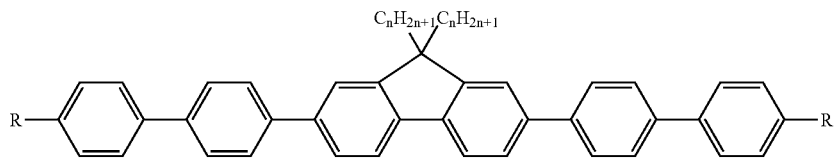

wherein n is from 2 to 10, preferably from 3 to 8 and as above, R has the general formula: X—S2-Y-Z and wherein X=O, CH$_2$ or NH and preferably X=O;

S2=linear or branched alkyl or alkenyl chain optionally including a heteroatom (e.g. O, S or NH) and preferably S2=a linear alkyl chain;

Y=O, CO$_2$ or S and preferably Y=CO$_2$; and

Z=a diene (end-group) and preferably Z=a 1,4, 1,5 or 1,6 diene.

Suitably, R is as for any of Compounds 3 to 6, as shown above.

A particular class of exemplary reactive mesogens has the formula:

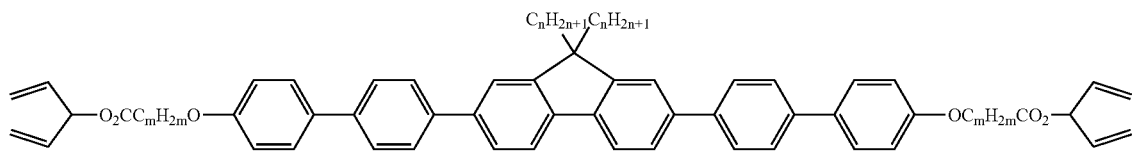

wherein:
n is from 2 to 10, preferably from 3 to 8; and
m is from 4 to 12, preferably from 5 to 11.

Still further suitable exemplary reactive mesogens have the general formula:

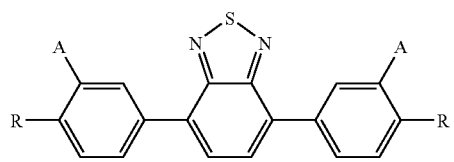

wherein A=H or F and wherein, as above, R has the general formula: X—S2-Y-Z and wherein
X=O, CH$_2$ or NH and preferably X=O;
S2=linear or branched alkyl or alkenyl chain optionally including a heteroatom (e.g. O, S or NH) and preferably S2=a linear alkyl chain;
Y=O, CO$_2$ or S and preferably Y=CO$_2$; and
Z=a diene (end-group) and preferably Z=a 1,4, 1,5 or 1,6 diene.

Suitably, R is as for any of Compounds 3 to 6, as shown above.

Particular exemplary reactive mesogens of this type have the formula:

In aspects, the photopolymerization process can be conducted at room temperature, thereby minimizing any possible thermal degradation of the reaction mesogen or polymer entities. Photopolymerization is also preferable to thermal polymerization because it allows subsequent sub-pixellation of the formed polymer by lithographic means.

Further steps may be conducted subsequent to the polymerization process including doping e.g. with photoactive dyes.

In preferred aspects, the polymerization process results in cross-linking e.g. to form a polymer network (e.g. an insoluble, cross-linked network).

Suitably, the light emitting polymer is a liquid crystal which can be aligned to emit polarised light. A suitable class of polymers is based on fluorene.

The reactive mesogen (monomer) typically has a molecular weight of from 400 to 2,000. Lower molecular weight monomers are preferred because their viscosity is also lower leading to enhanced spin coating characteristics and shorter annealing times which aids processing. The light emitting polymer typically has a molecular weight of above 4,000, typically 4,000 to 15,000.

The light emitting polymer (network) typically comprises from 5 to 50, preferably from 10 to 30 monomeric units.

According to another aspect of the present invention there is provided a process for applying a light emitting polymer to a surface comprising applying a reactive mesogen (as defined above) to said surface; and photopolymerizing said reactive mesogen in situ to form the light emitting polymer.

(Compound 16)

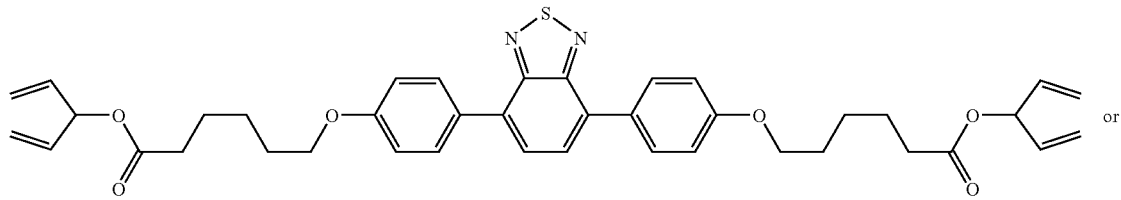

or (Compound 17)

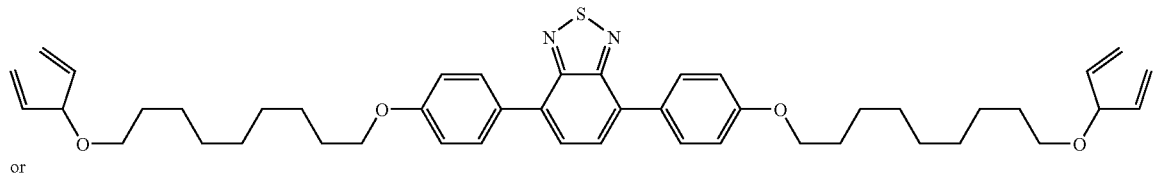

or (Compound 18)

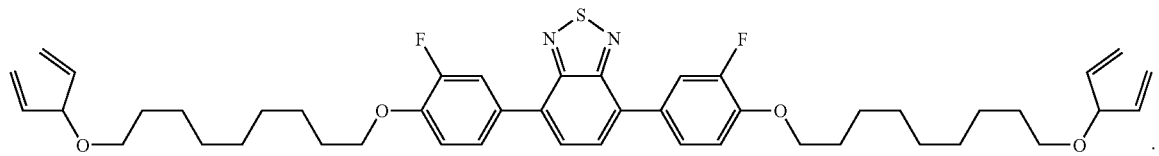

The light emitter polymers herein can in one aspect be used in a light emitter for a display comprising a photoalignment layer; and aligned on said photoalignment layer, the light emitting polymer.

The polymerization process herein can in one aspect be configured to form the light emitter by in situ polymerization of the reactive mesogens after their deposition on the photoalignment layer by any suitable deposition process including a spin-coating process The photoalignment layer typically comprises a chromophore attached to a sidechain polymer backbone by a flexible spacer entity. Suitable chromophores include cinnamates or coumarins, including derivatives of 6 or 7-hydroxycoumarins. Suitable flexible spacers comprise unsaturated organic chains, including e.g. aliphatic, amine or ether linkages.

An exemplary photoalignment layer comprises the 7-hydroxycoumarin compound having the formula:

(Compound 1)

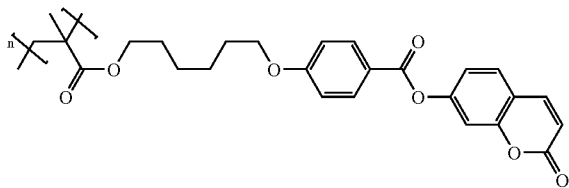

Other suitable materials for use in photoalignment layers are described in M. O'Neill and S. M. Kelly, J. Phys. D Appl. Phys. [2000], 33, R67.

In aspects, the photoalignment layer is photocurable. This allows for flexibility in the angle in the azimuthal plane at which the light emitting polymer (e.g. as a liquid crystal) is alignable and thus flexibility in its polarization characteristics.

The photalignment layer may also be doped with a hole transport compound, that is to say a compound which enables transport of holes within the photoalignment layer, such as a triarylamine. Examples of suitable triarylamines include those described in C. H. Chen, J. Shi, C. W. Tang, Macromol Symp. [1997] 125, 1.

An exemplary hole transport compound is 4,4',4"-tris[N-(1-napthyl)-N-phenylamino]triphenylamine which has the formula:

(Compound 2)

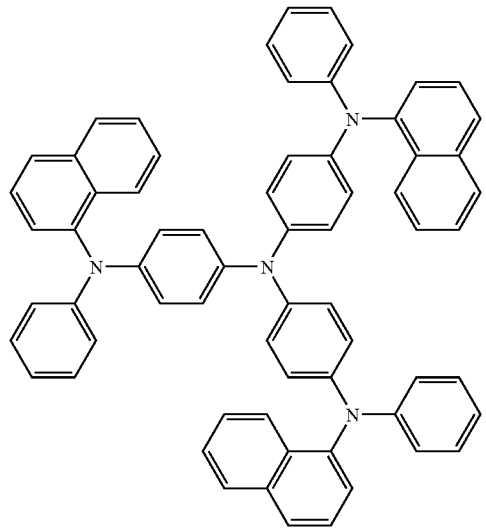

In aspects, the hole transport compound has a tetrahedral (pyramidal) shape which acts such as to controllably disrupt the alignment characteristics of the layer.

In one aspect, the photoalignment layer includes a copolymer incorporating both linear rod-like hole-transporting and photoactive side chains.

The light emitting polymer is aligned on the photoalignment layer. Suitably, the photoaligned polymer comprises uniaxially aligned chromophores. Typically polarization ratios of 30 to 40 are required, but with the use of a clean up polarizer ratios of 10 or more can be adequate for display uses.

In one aspect, the light emitter also comprises an organic light emitting diode (OLED) such as described in S. M. Kelly, Flat Panel Displays: Advanced Organic Materials, RSC Materials Monograph, ed. J. A. Connor, [2000]; C. H. Chen, J. Shi, C. W. Tang, Macromol Symp. [1997] 125, 1; R. H. Friend, R. W. Gymer, A. B. Holmes, J. H. Burroughes, R. N. Marks, C. Taliani, D. D. C. Bradley, D. A. Dos Santos, J. L. Bredas, M. Logdlund, W. R. Salaneck, Nature [1999] 397, 121; M. Grell, D. D. C. Bradley, Adv. Mater. [1999] 11, 895; N. C. Greenman, R. H. Friend Solid State Phys. [1995] 49, 1.

OLEDs may be configured to provide polarized electroluminescence.

The light emitting polymer may be aligned by a range of methods including mechanical stretching, rubbing, and Langmuir-Blodgett deposition. Mechanical alignment methods can however lead to structural degradation. The use of rubbed polyimide is a suitable method for aligning the light emitting polymer especially in the liquid crystal state. However, standard polyimide alignment layers are insulators, giving rise to low charge injection for OLEDs.

The susceptibility to damage of the alignment layer during the alignment process can be reduced by the use of a non-contact photoalignment method. In such methods, illumination with polarized light introduces a surface anisotropy to the alignment layer and hence a preferred in-plane orientation to the overlying light emitting polymer (e.g. in liquid crystal form).

The aligned light emitting polymer is in one aspect in the form of an insoluble nematic polymer network. Cross-linking has been found to improve the photoluminescence properties.

M. O'Neill, S. M. Kelly J. Appl. Phys. D [2000] 33, R67 provides a review of photalignment materials and methods.

The light emitter herein may comprise additional layers such as carrier transport layers. The presence of an electron-transporting polymer layer (e.g. comprising an oxadiazole ring) has been found to increase electroluminescence.

An exemplary electron transporting polymer has the formula:

(Compound 7)

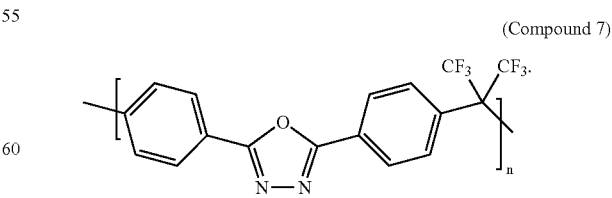

Pixellation of the light emitter may be achieved by selective photopatterning to produce red, green and blue pixels as desired. The pixels are typically rectangular in shape. The pixels typically have a size of from 1 to 50 μm, For microdisplays the pixel size is likely to be from 1 to 50 µm, preferably from 5 to 15 µm, such as from 8 to 10 µm. For other displays, larger pixel sizes e.g. 300 µm are more suitable.

In one preferred aspect, the pixels are arranged for polarized emission. Suitably, the pixels are of the same color but have their polarization direction in different orientations. To the naked eye this would look like one color, but when viewed through a polarizer some pixels would be bright and others less bright thereby giving an impression of 3D viewing when viewed with glasses having a different polarization for each eye.

The layers may also be doped with photoactive dyes. In aspects, the dye comprises a dichroic or pleachroic dye. Examples include anthraquinone dyes or tetralines, including those described in S. M. Kelly, Flat Panel Displays: Advanced Organic Materials, RSC Materials Monograph, ed. J. A. Connor, [2000]. Different dopant types can be used to obtain different pixel colors.

Pixel color can also be influenced by the choice of chromophore with different chromophores having more suitability as red, green or blue pixels, for example using suitably modified anthraquinone dyes.

Multicolor emitters are envisaged herein comprising arrangements or sequences of different pixel colors.

One suitable multicolor emitter comprises stripes of red, green and blue pixels having the same polarization state. This may be used as a sequential color backlight for a display which allows the sequential flashing of red, green and blue lights. Such backlights can be used in transmissive and reflective FLC displays where the FLC acts as a shutter for the flashing colored lights.

Another suitable multicolor emitter comprises a full color pixelated display in which the component pixels thereof have the same or different alignment.

Suitable multicolor emitters may be formed by a sequential 'coat, selective cure, wash off' process in which a first color emitter is applied to the aligned layer by a suitable coating process (e.g. spin coating). The coated first color emitter is then selectively cured only where pixels of that color are required. The residue (of uncured first color emitter) is then washed off. A second color emitter is then applied to the aligned layer, cured only where pixels of that color are required and the residue washed off. If desired, a third color may be applied by repeating the process for the third color.

The above process may be used to form a pixelated display such as for use in a color emissive display. This process is simpler than traditional printing (e.g. ink jet) methods of forming such displays.

There is also provided a backlight for a display comprising a power input; and a light emitter as described hereinbefore.

The backlight may be arranged for use with a liquid crystal display. In aspects, the backlight may be monochrome or multicolor.

There is further provided a display comprising a screen; and a light emitter or backlight as described hereinbefore.

The screen may have any suitable shape or configuration including flat or curved and may comprise any suitable material such as glass or a plastic polymer.

The light source of the present invention has been found to be particularly suitable for use with screens comprising plastic polymers such as polyethylene or polyethylene terephthalate (PET).

The display is suitable for use in consumer electronic goods such as mobile telephones, hand-held computers, watches and clocks and games machines.

There is further provided a security viewer (e.g. in kit form) comprising a light emitter as described herein in which the pixels are arranged for polarized emission; and view glasses having a different polarization for each eye.

There is further provided a method of forming a light emitter for a display comprising forming a photoalignment layer; and aligning a light emitting polymer on said photoalignment layer.

There is further provided a method of forming a light emitter for a display comprising forming a photoalignment layer; aligning a light emitting reactive mesogen on said photoalignment layer; and forming a light emitting polymer (network) by photopolymerisation of said reactive mesogen.

There is further provided a method of forming a multicolor emitter comprising applying a first color light emitter to the photoalignment layer; selectively curing said first color light emitter only where that color is required; washing off any residue of uncured first color emitter; and repeating the process for a second and any subsequent light color emitters.

All references herein are incorporated by reference in their entirety.

BRIEF DESCRIPTION OF THE DRAWINGS

Embodiments of systems according to the invention will now be described with reference to the accompanying experimental detail and drawings in which.

DETAILED DESCRIPTION OF PREFERRED EMBODIMENTS

General Experimental Details

Figure 1:
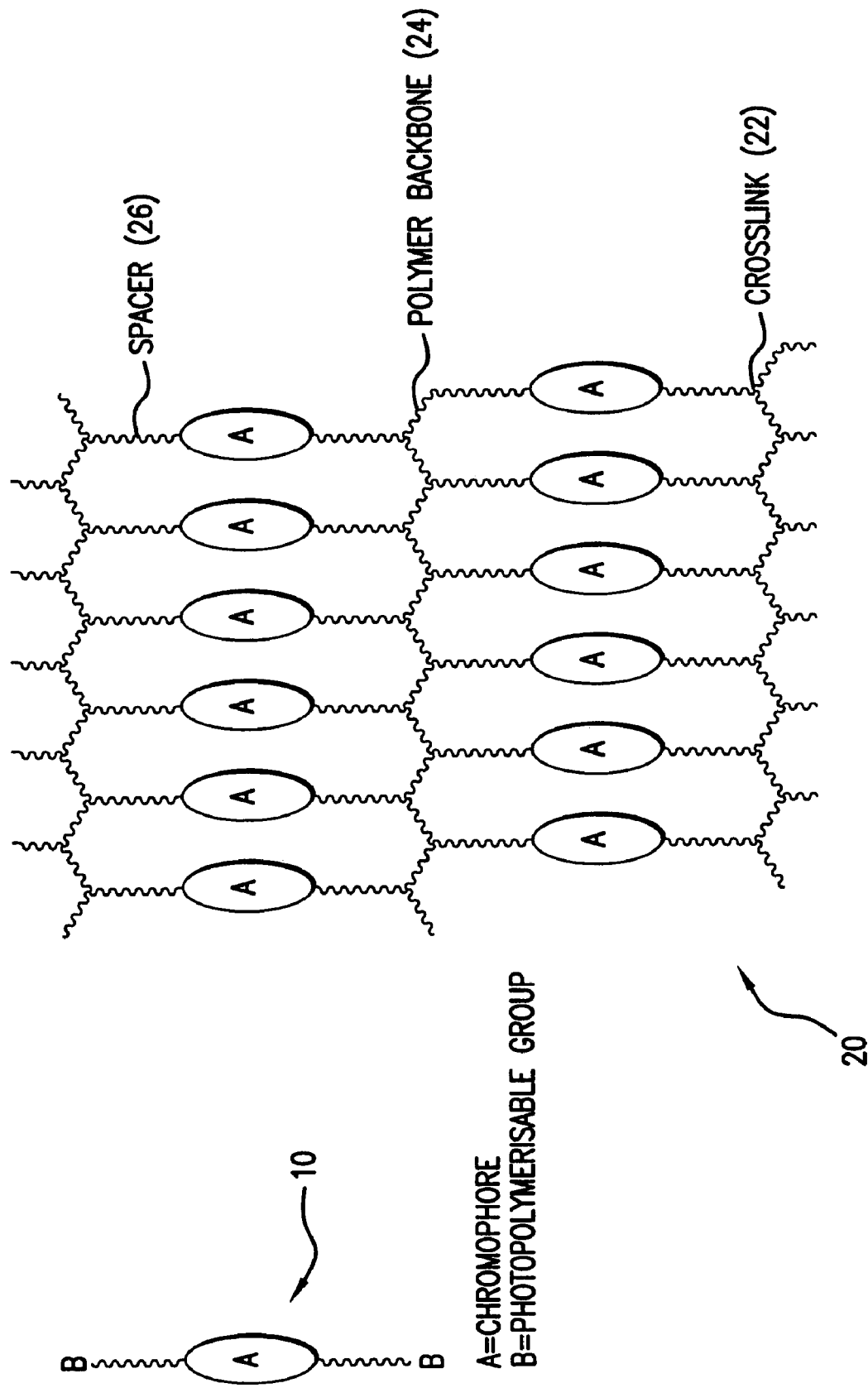
FIG. 1 is a schematic representation of a polymerization process herein.

Fluorene, 2-(tributylstanyl)thiophene, 4-(methoxyphenyl) boronic acid and the dienes were purchased from Aldrich and used as received. Reagent grade solvents were dried and purified as follows. N,N-Dimethylformamide (DMF) was dried over anhydrous $P_2O_5$ and purified by distillation. Butanone and methanol were distilled and stored over 5 Å molecular sieves. Triethylamine was distilled over potassium hydroxide pellets and then stored over 5 Å molecular sieves. Dichloromethane was dried by distillation over phosphorus pentoxide and then stored over 5 Å molecular sieves. Chloroform was alumina-filtered to remove any residual ethanol and then stored over 5 Å molecular sieves. $^1$H nuclear magnetic resonance (NMR) spectra were obtained using a JOEL JMN-GX270 FT nuclear resonance spectrometer. Infra-red (IR) spectra were recorded using a Perkin Elmer 783 infra-red spectrophotometer. Mass spectral data were obtained using a Finnegan MAT 1020 automated GC/MS. The purity of the reaction intermediates was checked using a CHROMPACK CP 9001 capillary gas chromatograph fitted with a 10 m CP-SIL 5CB capillary column. The purity of the final products was determined by high-performance liquid chromatography [HPLC] (5 µm, 25 cm×0.46 cm, ODS Microsorb column, methanol, >99%) and by gel-permeation chromatography [GPC] (5 µm, 30 cm×0.75 cm, 2× mixed D PL columns, calibrated using polystyrene standards [molecular weights=1000-4305000], toluene; no monomer present). The polymers were found to exhibit moderate to high $M_w$ values (10,000-30,000) and acceptable $M_w/M_n$ values (1.5-3). The liquid crystalline transition temperatures were determined using an Olympus BH-2 polarising light microscope together with a Mettler FP52 heating stage and a Mettler FP5 temperature control unit. The thermal analysis of the photopolymerisable monomers (Compounds 3 to 6) and the mainchain polymer (Compound 7) was carried out by a Perkin-Elmer Perkin-Elmer DSC 7 differential scanning calorimeter in conjunction with a TAC 7/3 instrument controller. Purification of intermediates and products was mainly accomplished by column chromatography using silica gel 60 (200-400 mesh) or aluminium oxide (Activated, Brockman 1, ~150 mesh). Dry flash column chromatography was carried out using silica gel H (Fluka, 5-40 µm). Electroluminescent materials were further purified by passing through a column consisting of a layer of basic alumina, a thin layer of activated charcoal, a layer of neutral alumina and a layer of Hi-Flo filter aid using DCM as an eluent. This was followed by recrystallisation from an ethanol-DCM mixture. At this stage, all glass-wear was thoroughly cleaned by rinsing with chromic acid followed by distilled water and then drying in an oven at 100° C. for 45 minutes. Purity of final products was normally confirmed by elemental analysis using a Fisons EA 1108 CHN apparatus.

Key intermediate 1: 2,7-bis[5-(4-hydroxyphenyl)thien-2-yl]-9,9-dipropylfluorene was synthesised as shown in Reaction Scheme 1. Full details each step are now given:

9-Propylfluorene: A solution of n-Butyllithium (18.0 cm$^3$, 10M solution in hexanes, 0.18 mol) was added slowly to a solution of fluorene (30.0 g, 0.18 mol) in THF (350 cm$^3$) at −50° C. The solution was stirred for 1 h at −75° C. and 1-bromopropane (23.0 g, 0.19 mol) was added slowly. The solution was allowed to warm to RT and then stirred for a further 1 h. Dilute hydrochloric acid (100 cm$^3$, 20%) and water (100 cm$^3$) were added and the product extracted into diethyl ether (3×150 cm$^3$). The ethereal extracts were dried (MgSO$_4$) and concentrated to a pale yellow oil (37.5 g, yield 100%). Purity 100% (GC).

$^1$H NMR (CD$_2$Cl$_2$) δ: 7.75 (2H, dd), 7.52 (2H, m), 7.32 (4H, m), 3.98 (1H, t), 1.95 (2H, m), 1.19 (2H, m), 0.85 (3H, t). IR (KBr pellet cm$^{-1}$): 3070 (m), 2962 (s), 1450 (s), 1296 (w), 1189 (w), 1030 (w), 938 (w), 739 (s). MS (m/z): 208 (M$^+$), 178, 165 (M100), 139.

9,9-Dipropylfluorene: A solution of n-Butyllithium (29.0 cm$^3$, 2.5M solution in hexanes, 0.073 mol) was added slowly to a solution of 9-propylfluorene (15.0 g, 0.072 mol) in THF at −50° C. The solution was stirred for 1 h at −75° C., 1-bromopropane (10.0 g, 0.092 mol) was added slowly and the temperature raised to RT after completion of the addition. After 18 h, dilute hydrochloric acid (20%, 100 cm$^3$) and water (100 cm$^3$) were added and the product extracted into diethyl ether (2□100 cm$^3$). The ethereal extracts were dried (MgSO$_4$) and concentrated to a pale brown oil which crystallised overnight at RT. The product was purified by recrystallisation from methanol to yield a white crystalline solid (14.5 g, yield 80%) mp 47-49° C. (Lit. 49-50° C.$^{19}$). Purity 100% (GC).

$^1$H NMR (CDCl$_3$) δ: 7.68 (2H, m), 7.31 (6H, m), 1.95 (4H, t), 0.65 (10H, m). IR (KBr pellet cm$^{-1}$): 3068 (m), 2961 (s), 1449 (s), 1293 (w), 1106 (w), 1027 (w), 775 (m), 736 (s), 637 (m). MS (m/z): 250 (M$^+$), 207 (M100), 191, 179, 165.

2,7-Dibromo-9,9-dipropylfluorene: Bromine (10.0 g, 0.063 mol) was added to a stirred solution of 9,9-dipropylfluorene (7.0 g, 0.028 mol) in chloroform (25 cm$^3$) and the solution purged with dry N$_2$ for 0.5 h. Chloroform (50 cm$^3$) was added and the solution washed with saturated sodium bisulphite solution (75 cm$^3$), water (75 cm$^3$), dried (MgSO$_4$) and concentrated to a pale yellow powder (11.3 g, yield 98%) mp 134-137° C.

$^1$H NMR (CDCl$_3$) δ: 7.51 (2H, d), 7.45 (4H, m), 1.90 (4H, t), 0.66 (10H, m). IR (KBr pellet cm$^{-1}$): 2954 (s), 1574 (w), 1451 (s), 1416 (m), 1270 (w), 1238 (w), 1111 (w), 1057 (s), 1006 (w), 931 (w), 878 (m), 808 (s), 749 (m). MS (m/z): 409 (M$^+$), 365, 336, 323, 284, 269, 256, 248, 202, 189, 176 (M100), 163.

2,7-bis(Thien-2-yl)-9,9-dipropylfluorene: A mixture of 2,7-dibromo-9,9-dipropylfluorene (6.0 g, 0.015 mol), 2-(tributylstannyl)thiophene (13.0 g, 0.035 mol) and tetrakis (triphenylphosphine)-palladium (0) (0.3 g, 2.6×10$^{-4}$ mol) in DMF (30 cm$^3$) was heated at 90° C. for 24 h. DCM (200 cm$^3$) was added to the cooled reaction mixture and the solution washed with dilute hydrochloric acid (2□150 cm$^3$, 20%), water (100 cm$^3$), dried (MgSO$_4$) and concentrated onto silica gel for purification by column chromatography [silica gel, DCM:hexane 1:1]. The compound was purified by recrystallisation from DCM: ethanol to yield light green crystals (4.3 g, yield 69%), mp 165-170° C. Purity 100% (GC).

$^1$H NMR (CDCl$_3$) δ: 7.67 (2H, d), 7.60 (2H, dd), 7.57 (2h, d), 7.39 (2H, dd), 7.29 (2H, dd), 7.11 (2H, dd), 2.01 (4H, m), 0.70 (10H, m). IR (KBr pellet cm$^{-1}$): 2962 (m), 2934 (m), 2872 (m), 1467 (m), 1276 (w), 1210 (m), 1052 (w), 853 (m), 817 (s), 691 (s). MS (m/z): 414 (M$^+$, M100), 371, 342, 329, 297, 207, 165.

2,7-bis(5-Bromothien-2-yl)-9,9-dipropylfluorene: N-Bromosuccinimide (2.1 g, 0.012 mol freshly purified by recrystallisation from water) was added slowly to a stirred solution of 2,7-bis(thien-2-yl)-9,9-dipropylfluorene (2.3 g, 5.55×10$^{-3}$ mol) in chloroform (25.0 cm$^3$) and glacial acetic acid (25.0 cm$^3$). The solution was heated under reflux for 1 h, DCM (100 cm$^3$) added to the cooled reaction mixture, washed with water (100 cm$^3$), HCl (150 cm$^3$, 20%), saturated aqueous sodium bisulphite solution (50 cm$^3$), and dried (MgSO$_4$). The solvent was removed in vacuo and the product purified by recrystallisation from an ethanol-DCM mixture to yield yellow-green crystals (2.74 g, yield 86%). mp 160-165° C.

$^1$H NMR (CDCl$_3$) δ: 7.66 (2H, d), 7.49 (2H, dd), 7.46 (2H, d), 7.12 (2H, d), 7.05 (2H, d), 1.98 (4H, t), 0.69 (10H, m). IR (KBr pellet cm$^{-1}$): 3481 (w), 2956 (s), 1468 (s), 1444 (m), 1206 (w), 1011 (w), 963 (w), 822 (m), 791 (s), 474 (w). MS (m/z): 572 (M$^+$), 529, 500, 487, 448, 433, 420, 407, 375, 250, 126.

2,7-bis[5-(4-Methoxyphenyl)thien-2-yl]-9,9-dipropylfluorene: A mixture of 2,7-bis(5-bromothien-2-yl)-9,9-dipropylfluorene (2.7 g, 4.7×10$^{-3}$ mol), 4-(methoxyphenyl) boronic acid (2.15 g, 0.014 mol), tetrakis (triphenylphosphine)palladium (0) (0.33 g, 2.9×10$^{-4}$ mol), sodium carbonate (3.0 g, 0.029 mol) and water (20 cm$^3$) in DME (100 cm$^3$) was heated under reflux for 24 h. More 4-(methoxyphenyl)boronic acid (1.0 g, 6.5×10$^{-3}$ mol) was added to the cooled reaction mixture, which was then heated under reflux for a further 24 h. DMF (20 cm$^3$) was added and the solution heated at 110° C. for 24 h, cooled and dilute hydrochloric acid (100 cm$^3$, 20%) added. The cooled reaction mixture was extracted with diethyl ether (250 cm$^3$) and the combined ethereal extracts washed with water (100 cm$^3$), dried (MgSO$_4$), and concentrated onto silica gel to be purified by column chromatography [silica gel, DCM:hexane 1:1] and recrystallisation from an ethanol-DCM mixture to yield a green crystalline solid (1.86 g, yield 63%), Cr—N, 235° C.; N—I, 265° C.

$^1$H NMR (CD$_2$Cl$_2$) δ: 7.71 (2H, dd), 7.61 (8H, m), 7.37 (2H, d), 7.24 (2H, d), 6.95 (4H, d), 3.84 (6H, s), 2.06 (4H, m), 0.71 (10H, m). IR (KBr pellet cm$^{-1}$): 2961 (w), 1610 (m), 1561 (m), 1511 (s), 1474 (s), 1441 (m), 1281 (m), 1242 (s), 1170 (s), 1103 (m), 829 (m), 790 (s). MS (m/z): 584 (M$^+$-C$_3$H$_7$), 569, 555, 539, 525, 511, 468, 313, 277 (M100), 248, 234. Elemental analysis. Calculated: wt % C=78.56%; H, 6.11%; S, 10.23%. Found: C, 78.64%; H, 6.14%; S, 10.25%.

2,7-bis[5-(4-Hydroxyphenyl)thien-2-yl]-9,9-dipropylfluorene): A 1M solution of boron tribromide in chloroform (9 cm$^3$, 9.0 mmol) was added dropwise to a stirred solution of 2,7-bis[5-(4-methoxyphenyl)thien-2-yl]-9,9-dipropylfluorene (1.3 g, 2.1×10$^{-3}$ mol) at 0° C. The temperature was allowed to rise to RT overnight and the solution added to ice-water (200 cm$^3$) with vigorous stirring. The product was extracted into diethyl ether (220 cm$^3$), washed with aqueous sodium carbonate (2M, 150 cm$^3$), dried (MgSO$_4$) and purified by column chromatography [silica gel DCM:diethyl ether:ethanol 40:4:1] to yield a green solid (1.2 g, yield 96%), Cr—I, 277° C.; N—I, 259° C.

$^1$H NMR (d-acetone) δ: 8.56 (2H, s), 7.83 (2H, dd), 7.79 (2H, d), 7.68 (2H, dd), 7.57 (4H, dd), 7.50 (2H, dd), 7.31 (2H, dd), 6.91 (4H, dd), 2.15 (4H, m), 0.69 (10H, m). IR (KBr pellet cm$^{-1}$): 3443 (s, broad), 2961 (m), 1610 (m), 1512 (m), 1474 (m), 1243 (m), 1174 (m), 1110 (w), 831 (m), 799 (s). MS (m/z): 598 (M$^+$), 526, 419 (M100), 337.

Compound 3: 2,7-bis(5-{4-[5-(1-Vinyl-allyloxycarbonyl)pentyloxy]phenyl}thien-2-yl)-9,9-dipropylfluorene: The 1,3-pentadiene monomer (Compound 3) was synthesised as depicted in Reaction Scheme 2. Full details of each step are now given:

1,4-Pentadien-3-yl 6-bromohexanoate: A solution of 6-bromohexanoyl chloride (3.2 g, 0.026 mol) in DCM (30 cm$^3$) was added dropwise to a solution of 1,4-pentadien-3-ol (2.0 g, 0.024 mol) and triethylamine (2.4 g, 0.024 mol) in DCM (30 cm$^3$). The mixture was stirred for 1 h and washed with dilute hydrochloric acid (20%, 50 cm$^3$), saturated potassium carbonate solution (50 cm$^3$), water (50 cm$^3$) then dried (MgSO$_4$) and concentrated to a brown oil. The product was purified by dry flash chromatography [silica gel, DCM] to yield a pale yellow oil (4.7 g, yield 75%). Purity>95% (GC).

$^1$H NMR (CDCl$_3$) δ: 5.82 (2H, m), 5.72 (1H, m), 5.30 (2H, d), 5.27 (2H, d), 3.42 (2H, t), 2.37 (2H, t), 1.93 (2H, m), 1.72 (2H, m), 1.54 (2H, m). IR (KBr pellet cm$^{-1}$): 3095 (w), 1744 (s), 1418 (w), 1371 (w), 12521 (m), 1185 s), 983 (m), 934 (m). MS (m/z): 261 (M$^+$), 177, 67.

2,7-bis(5-{4-[5-(1-Vinyl-allyloxycarbonyl)pentyloxy]phenyl}thien-2-yl)-9,9-dipropylfluorene: A mixture of 2,7-bis[5-(4-hydroxyphenyl)thien-2-yl]-9,9-dipropylfluorene (0.6 g, 1.0×10$^{-3}$ mol), 1,4-pentadien-3-yl 5-bromohexanoate (0.7 g, 2.7×10$^{-3}$ mol) and potassium carbonate (0.5 g, 3.6×10$^{-3}$ mol) in acetonitrile (25 cm$^3$) was heated at 50° C. for 18 h. The mixture was then heated under reflux conditions for a further 20 h. Excess potassium carbonate was filtered off and precipitated product rinsed through with DCM (230 cm$^3$). The solution was concentrated onto silica gel for purification by column chromatography [silica gel, DCM:hexane 1:1 gradients to DCM] and recrystallisation from a DCM-ethanol mixture to yield a green-yellow solid (0.4 g, yield 40%), Cr—N, 92° C.; N—I, 108° C.

$^1$H NMR (CD$_2$Cl$_2$) δ: 7.69 (2H, d), 7.58 (8H, m), 7.35 (2H, d), 7.22 (2H, d), 6.91 (4H, d), 5.83 (4H, m), 5.68 (2H, m), 5.29 (2H, t), 5.25 (2H, t), 5.21 (2H, t), 5.19 (2H, t), 3.99 (4H, t), 2.37 (4H, t), 2.04 (4H, m), 1.80 (4H, quint), 1.70 (4H, quint), 1.51 (4H, quint) 0.69 (10H, m). IR (KBr pellet cm$^{-1}$): 2936 (m), 2873 (m), 1738 (s), 1608 (m), 1511 (m), 1473 (s), 1282 (m), 1249 (s), 1177 (s), 1110 (m), 982 (m), 928 (m), 829 (m), 798 (s). APCI-MS (m/z): 958 (M$^+$), 892 (M100). Elemental analysis. Calculated: wt % C=76.37, wt % H=6.93, wt % S=6.68. Found: wt % C=75.93, wt % H=6.95, wt % S=6.69.

Compound 4: 2,7-bis(5-{(4-[5-(1-Allylbut-3-enyloxycarbonyl)pentyloxy]phenyl}thien-2-yl)-9,9-dipropylfluorene:

The 1,3-heptadiene monomer (Compound 4) was synthesised as depicted in reaction Scheme 3. Full details of each step are now given:

1,6-Heptadien-5-yl 5-bromopentanoate: 5-Bromopentanoyl chloride (3.0 g, 0.015 mol) was added dropwise to 1,6-heptadien-4-ol (1.5 g, 0.013 mol) and triethylamine (1.4 g, 0.014 mol) in DCM (25 cm$^3$). The mixture was stirred for 2 h and washed with dilute hydrochloric acid (20%, 50 cm$^3$), saturated aqueous potassium carbonate solution (50 cm$^3$), water (50 cm$^3$) then dried (MgSO$_4$) and concentrated to a brown oil. The product was purified by dry flash chromatography [silica gel, DCM] to yield a pale yellow oil (1.7 g, yield 48%). Purity>92% (GC).

$^1$H NMR (CDCl$_3$) δ: 5.74 (2H, m), 5.08 (4H, m), 4.99 (1H, m), 3.41 (2H, t), 2.31 (6H, m), 1.88 (2H, m), 1.76 (2H, m). IR (Film cm$^{-1}$): 2952 (m), 1882 (w), 1734 (s), 1654 (m) 1563 (w), 1438 (m), 1255 (m), 1196 (s), 996 (m), 920 (s). MS (m/z): 275 (M$^+$), 245, 219, 191, 183, 163 (M100), 135, 95, 79.

2,7-bis(5-{4-[5-(1-Allylbut-3-enyloxycarbonyl)pentyloxy]phenyl}thien-2-yl)-9,9-dipropylfluorene: A mixture of 2,7-bis[5-(4-hydroxyphenyl)thien-2-yl]-9,9-dipropylfluorene (0.3 g, 1.0×10$^{-3}$ mol), 1,6-heptadienyl 6-bromohexanoate (0.7 g, 2.7×10$^{-3}$ mol) and potassium carbonate (0.5 g, 3.6×10$^{-3}$ mol) in acetonitrile (25 cm$^3$) was heated under reflux for 20 h. Excess potassium carbonate was filtered off and precipitated product rinsed through with DCM (230 cm$^3$). The solution was concentrated onto silica gel for purification by column chromatography [silica gel, DCM:hexane 1:1 gradients to DCM] and recrystallisation from a DCM-ethanol mixture to yield a green-yellow solid (0.21 g, yield 21%), Cr—I, 97° C., N—I, 94° C.

$^1$H NMR (CDCl$_3$) δ: 7.68 (2H, d), 7.60 (2H, dd), 7.58 (2H, d), 7.57 (2H, d), 7.33 (2H, d), 7.20 (2H, d), 6.91 (2H, d), 5.75 (4H, m), 5.08 (8H, m), 5.00 (2H, quint), 4.00 (4H, t), 2.33 (12H, m), 2.02 (4H, t), 1.82 (4H, quint), 1.71 (4H, quint), 1.53 (4H, m), 0.72 (10H, m). IR (KBr pellet cm$^{-1}$): 3443 (s), 2955 (s), 1734 (s), 1643 (w), 1609 (m), 1512 (m), 1473 (s), 1249 (s), 1178 (s), 996 (m), 918 (m), 829 (m), 799 (s). APCI-MS (m/z): 1015 (M+, M100), 921. Elemental analysis. Calculated: wt % C=76.89, wt % H=7.35, wt % S=6.32%. Found: wt % C=76.96, wt % H=7.42, wt % S=6.23.

Compound 5: 2,7-bis(5-{4-[3-(1-Vinylallyloxycarbonyl)propyloxy]phenyl}thien-2-yl)-9,9-dipropylfluorene The 1,3-pentadiene homologue (Compound 5) was synthesised as depicted in reaction Scheme 4. Full details of each step are now given:

4-Bromobutanoyl chloride: Oxalyl chloride (15.2 g, 0.12 mol) was added dropwise to a stirred solution of 4-bromobutanoic acid (10.0 g, 0.060 mol) and DMF (few drops) in chloroform (30 cm$^3$). The solution was stirred overnight under anhydrous conditions and concentrated to a pale brown oil which was filtered to remove solid impurities (11.0 g, yield 99%).

1,4-Pentadien-3-yl 4-bromobutanoate: 4-Bromobutanoyl chloride (3.0 g, 0.016 mol) was added dropwise to a solution of 1,4-pentadien-3-ol (1.3 g, 0.015 mol) and triethylamine (1.5 g, 0.015 mol) in DCM (30 cm$^3$). The solution was stirred for 2 h and washed with dilute hydrochloric acid (20%, 50 cm$^3$), saturated potassium carbonate solution (50 cm$^3$), water (50 cm$^3$) then dried (MgSO$_4$) and concentrated to a pale brown oil. The product was purified by dry flash chromatography [silica gel, DCM] to yield a pale yellow oil (1.8 g, yield 51%). Purity>85% (GC; decomposition on column).

$^1$H NMR (CDCl$_3$) δ: 5.83 (2H, m), 5.72 (1H, m), 5.27 (4H, m), 3.47 (2H, t), 2.55 (2H, t), 2.19 (2H, quint). IR (KBr pellet cm$^{-1}$): 3096 (w), 2973 (w), 1740 (s), 1647 (w), 1419 (m), 1376 (m), 1198 (s), 1131 (s), 987 (s), 932 (s), 557 (w). MS (m/z): 217, 166, 152, 149, 125, 110, 84, 67 (M100).

2,7-bis(5-{4-[3-(1-Vinylallyloxycarbonyl)propyloxy] phenyl}thien-2-yl)-9,9-dipropylfluorene: A mixture of 2,7-bis[5-(4-hydroxyphenyl)thien-2-yl]-9,9-dipropylfluorene (0.25 g, 4.2×10$^{-4}$ mol), 1,4-pentadien-3-yl 4-bromobutanoate (0.40 g, 1.7×10$^{-3}$ mol) and potassium carbonate (0.20 g, 1.4×10$^{-3}$ mol) in DMF (10 cm$^3$) was heated under reflux for 4 h. The cooled solution was filtered, rinsed through with DCM (3×20 cm$^3$) and concentrated to a pale green oil which was purified by column chromatography [silica gel, DCM:hexane 2:1] followed by recrystallisation from ethanol:DCM to yield a green-yellow powder (0.20 g, yield 53%), Cr—N, 92° C.; N—I, 116° C.

$^1$H NMR (CDCl$_3$) δ: 7.61 (10H, m), 7.33 (2H, d), 7.20 (2H, d), 6.92 (4H, d), 5.85 (4H, m), 5.74 (2H, m), 5.32 (4H, d, J=17 Hz), 5.24 (4H, d, J=10 Hz), 4.06 (4H, t), 2.56 (4H, t), 2.16 (4H, quint), 2.05 (4H, t), 0.72 (10H, m). IR (KBr pellet cm$^{-1}$): 3449 (m), 2960 (m), 1738 (s), 1609 (m), 1512 (m), 1473 (s), 1380 (w), 1249 (m), 1174 (s), 1051 (m), 936 (m), 830 (m), 799 (s). APCI-MS (m/z): 903 (M$^+$), 837 (M100), 772. Elemental analysis. Calculated: wt % C=75.80, wt % H=6.47, wt % S=7.10. Found: wt % C=76.13, wt % H=6.48%, wt % S=6.91.

Compound 6: 2,7-bis{5-[4-(8-Diallylaminooctyloxy)phenyl]-thien-2-yl}-9,9-dipropylfluorene The method of preparation of the N,N-diallylamine monomer (Compound 6) is shown in reaction Scheme 5. Full details of each step are now given:

8-Diallylaminooctan-1-ol. A mixture of 8-bromooctan-1-ol (10.0 g, 0.048 mol), diallylamine (4.85 g, 0.050 mol) and potassium carbonate (7.0 g, 0.051 mol) in butanone (100 cm$^3$) was heated under reflux for 18 h. Excess potassium carbonate was filtered off and the solution concentrated to a colourless oil. The product was purified by dry flash chromatography [silica gel, DCM:ethanol 4:1]. (10.0 g, yield 93%)

$^1$H NMR (CDCl$_3$) δ: 5.86 (2H, d), 5.14 (4H, m), 3.71 (4H, quart), 3.63 (4H, t), 3.09 (4H, d), 1.56 (4H, m), 1.45 (2H, quint), 1.30 (6H, m). IR (KBr pellet cm$^{-1}$): 3344 (s), 2936 (s), 1453 (w), 1054 (m), 998 (m), 921 (m). MS (m/z): 225 (M$^+$), 198, 184, 166, 152, 138, 124, 110 (M100), 81.

Toluene-4-sulphonic acid 8-diallylaminooctyl ester. 4-Toluene-sulphonyl chloride (12.5 g, 0.066 mol) was added slowly to a stirred solution of 8-diallylaminooctan-1-ol (10.0 g, 0.044 mol) and pyridine (7.0 g, 0.088 mol) in chloroform (100 cm$^3$) at 0° C. After 24 h, water (100 cm$^3$) was added and the solution washed with dilute hydrochloric acid (20%, 100 cm$^3$), sodium carbonate solution (100 cm$^3$), water (100 cm$^3$), dried (MgSO$_4$) and concentrated to a yellow oil which was purified by column chromatography [silica gel, 4% diethyl ether in hexane eluting to DCM:ethanol 10:1] to yield the desired product (6.7 g, yield 40%).

$^1$H NMR (CDCl$_3$) δ: 7.78 (2H, d), 7.34 (2H, d), 5.84 (2H, m), 5.13 (4H, m), 4.01 (2H, t), 3.41 (4H, d), 2.45 (3H, s), 2.39 (2H, t), 1.63 (2H, quint), 1.42 (2H, quint), 1.30 (2H, quint), 1.23 (6H, m). IR (KBr pellet cm$^{-1}$): 3454 (w), 2957 (m), 1453 (s), 1402 (m), 1287 (m), 1159 (w), 1061 (m), 914 (w), 878 (m), 808 (s), 448 (m). MS (m/z): 380 (M$^+$), 364, 352, 338, 224, 110 (M100), 91, 79, 66.

2,7-bis{5-[4-(8-Diallylaminooctyloxy)phenyl]-thien-2-yl}-9,9-dipropylfluorene: A mixture of 2,7-bis[5-(4-hydroxyphenyl)thien-2-yl]-9,9-dipropylfluorene (0.5 g, 8.4×10$^{-4}$ mol), toluene-4-sulphonic acid-8-diallylaminooctyl ester (0.8 g, 2.1×10$^{-3}$ mol) and potassium carbonate (0.3 g, 2.2×10 3 mol) in butanone (30 cm$^3$) was heated under reflux for 24 h. Excess potassium carbonate was filtered off and rinsed with DCM (3×30 cm$^3$). The solution was concentrated onto silica gel for purification by column chromatography [silica gel, DCM:hexane 2:1 eluting to DCM:ethanol 4:1]. The product was obtained as a yellow-green glass (0.35 g, yield 41%), N—I, 95° C.

$^1$H NMR (CDCl$_3$) δ: 7.67 (2H, d), 7.58 (8H, m), 7.34 (2H, d), 7.20 (2H, d), 6.92 (4H, d), 5.94 (4H, m), 5.25 (8H, m), 3.99 (4H, t), 3.22 (8H, d), 2.02 (4H, t), 1.80 (4H, quint), 1.56 (4H, quint), 1.47 (4H, quint), 1.35 (12H, m), 0.71 (10H, m). IR (KBr pellet cm$^{-1}$): 3437 (s), (2934 (s), 1609 (s), 1512 (s), 1472 (s), 1283 (m), 1249 (s), 1179 (s), 1031 (w), 918 (w), 829 (m), 798 (s). APCI-MS (m/z): 1014 (M$^+$, M100), 973. Elemental analysis. Calculated: wt % C=79.40, wt % H=8.35, wt % N=2.76, wt % S=6.33. Found: wt % C=79.33, wt % H=8.29, wt % N=2.88, wt % S=6.17.

Compound 7: poly(phenylene-1,3,4-oxadiazole-phenylene-hexafluoropropylene)

The electron-transporting polymer (Compound 7) was prepared according to a literature method described in Li, X.-C.; Kraft, A.; Cervini, R.; Spencer, G. C. W.; Cacialli, F.; Friend, R. H.; Gruener, J.; Holmes, A. B.; de Mello, J. C.; Moratti, S. C. Mat. Res. Symp. Proc. 1996, 413 13.

In more detail the preparation details were as follows: A solution of 4,4'-(hexafluoroisopropylidine)bis(benzoic acid) (2.54 g, 6.48×10$^{-3}$ mol) and hydrazine sulphate (0.84 g, 6.48×10$^{-3}$ mol) in Eaton's reagent (25 cm$^3$) was heated under reflux for 18 h. The cooled solution was added to brine (300 cm$^3$) and the product extracted into chloroform (8×200 cm$^3$). The organic extracts were combined, dried (MgSO$_4$) and the solvent removed under reduced pressure to yield the crude product which was purified by dissolving in a minimum volume of chloroform and precipitating by dropwise addition to methanol (1000 cm$^3$). The precipitate was filtered off and washed with hot water before being dried in vacuo. The precipitation was repeated a further three times washing with methanol each time. The product was then dissolved in chloroform and passed through a microfilter (0.45 μm). The pure product was then precipitated in methanol (500 cm$^3$) and the methanol removed under reduced pressure to yield a white fibrous solid which was dried in vacuo. Yield 1.26 g (50%).

$^1$H NMR (CDCl$_3$) δ$_H$: 8.19 (4H/repeat unit, d), 7.61 (4H/repeat unit, d). IR $v_{max}$/cm$^{-1}$: 3488 (m), 1621 (m), 1553 (m), 1502 (s), 1421 (m), 1329 (m), 1255 (m), 1211 (s), 1176 (s), 1140 (s), 1073 (m), 1020 (m), 969 (m), 929 (m), 840 (m), 751 (m), 723 (s). GPC: $M_w$:$M_n$=258211:101054.

An alternative electron-transport copolymer is prepared according to the method described in Xiao-Chang Li et al J. Chem. Soc. Chem. Commun., 1995, 2211.

In more detail the preparation details were as follows: Terephthaloyl chloride (0.50 g, 2.46×10$^{-3}$ mol) was added to hydrazine hydrate (50 cm$^3$) at room temperature and the mixture stirred for 2 h. The precipitate was filtered off, washed with water (100 cm$^3$) and dried in vacuo. The crude hydrazide (0.25 g, 1.3×10$^{-3}$ mol), 4,4'-(hexafluoroisopropylidine)bis(benzoic acid) (2.50 g, 6.4×10$^{-3}$ mol) and hydrazine sulphate (0.66 g, 5.2×10$^{-3}$ mol) were added to Eaton's reagent and the resultant mixture heated at 100° C. for 24 h. The reaction mixture was added to water (300 cm$^3$) and the product extracted into chloroform (3×300 cm$^3$). The organic extracts were combined, dried (MgSO$_4$) and the solvent removed in vacuo before re-dissolving the product in the minimum volume of chloroform. The solution was added dropwise to methanol (900 cm$^3$) to give a white precipitate which was filtered off and dried in vacuo. The precipitation was repeated twice before dissolving the product in chloroform and passing through a microfilter (0.45 μm) into methanol (500 cm$^3$). The methanol was removed under reduced pressure and the product dried in vacuo. Yield 1.1 g (41%)

$^1$H NMR (CDCl$_3$) $\delta_H$: 8.18 (dd, 4H/repeat unit), 7.60 (dd, 4H/repeat unit). IR $\nu_{max}$/cm$^{-1}$: 3411 (w), 2366 (w), 1501 (m), 1261 (s), 1211 (s), 1176 (s), 1140 (m), 1072 (m), 1021 (w), 968 (m), 931 (w), 840 (m), 722 (m). GPC: $M_w$:$M_n$=20572:8320.

Key intermediate 2: 9,9-diethyl-2,7-bis(4-hydroxybiphenyl-4'-yl)fluorene was synthesised as shown in Reaction Scheme 7. Full details of each step are now given:

9-Ethylfluorene: A solution of n-butyllithium (79.52 cm$^3$, 0.2168 mol, 2.5M in hexane) was added slowly to a solution of fluorene (30.00 g, 0.1807 mol) in THF (300 cm$^3$) at −70° C. The solution was stirred for 1 hour at −75° C. and 1-bromoethane (17.59 cm$^3$, 0.2349 mol) was added slowly. The solution was allowed to warm to room temperature and then stirred overnight. Dilute hydrochloric acid (200 ml, 20%) was added to the reaction mixture and stirred for a further 10 minutes. Water (250 cm$^3$) was added and the product extracted into diethyl ether (3×300 cm$^3$). The combined organic extracts were dried (MgSO$_4$) and the solvent removed on a rotary evaporator. The resulting oil was purified by distillation to yield a pale yellow oil (25.00 g, 71%, b.pt.—150° C. @ 1 mbar Hg).

$^1$H NMR (DMSO) δ: 7.70 (2H, m), 7.50 (2H, m), 7.30 (4H, m), 4.00 (1H, t), 2.02 (2H, quart), 0.31 (3H, t). IR $\nu_{max}$/cm$^{-1}$: 3072 (m), 2971, 1618, 1453, 1380, 1187, 759, 734. MS m/z: 170 (M$^+$), 94, 82, 69.

9,9-Diethylfluorene: A solution of n-butyllithium (77.34 cm$^3$, 0.1934 mol, 2.5M in hexane) was added slowly to a solution of 9-ethylfluorene (25.00 g, 0.1289 mol) in THF (250 cm$^3$) at −70° C. The solution was stirred for 1 hour at −75° C. and 1-bromoethane (17.59 cm$^3$, 0.1934 mol) was added slowly. The solution was allowed to warm to room temperature and then stirred overnight. Dilute hydrochloric acid (200 cm$^3$, 20%) was added to the reaction mixture and stirred for a further 10 minutes. Water (250 cm$^3$) was added and the product extracted into diethyl ether (3×300 cm$^3$). The combined organic extracts were dried (MgSO$_4$) and the solvent removed on a rotary evaporator. The resulting oil was cooled to room temperature and recrystallised with ethanol to yield white crystals (19.50 g, 68%, m.pt. 60-62° C.).

$^1$H NMR (DMSO) δ: 7.76 (2H, m), 7.51 (2H, m), 7.35 (4H, m), 1.51 (4H, quart), 0.30 (6H, t), IR $\nu_{max}$/cm$^{-1}$: 3069, 2972, 1612, 1448, 1310, 761, 736. MS m/z: 222 (M$^+$), 193, 152, 94, 82, 75.

2,7-Dibromo-9,9-diethylfluorene: Bromine (13.47 cm$^3$, 0.2568 mol) was added to a stirred solution of 9,9-diethylfluorene (19.00 g, 0.0856 mol) in DCM (250 cm$^3$). The HBr gas evolved was passed through a scrubbing solution of NaOH (1.5M). The reaction mixture was stirred for 4 hours. The reaction mixture was washed with sodium metabisulphite solution and extracted into diethyl ether (3×300 cm$^3$). The combined organic extracts were dried and the solvent removed on a rotary evaporator. The crude product was recrystallised from ethanol to yield a white crystalline solid (20.00 g, 61%, m.pt. 152-154° C.).

$^1$H NMR (DMSO) δ: 7.52 (2H, m), 7.45 (4H, m), 1.99 (4H, quart), 0.31 (6H, t). IR $\nu_{max}$/cm$^{-1}$: 2966, 1599, 1453, 1418, 1058, 772, 734. MS m/z: 380 (M$^+$), 351, 272, 220, 189, 176, 165, 94, 87, 75.

4-Bromo-4'-octyloxybiphenyl: A mixture of 4-bromo-4'-hydroxybiphenyl (50.00 g, 0.2008 mol), 1-bromooctane (50.38 g, 0.2610 mol), potassium carbonate (47.11 g, 0.3414 mol) and butanone (500 cm$^3$) was heated under reflux overnight. The cooled mixture was filtered and the solvent removed on a rotary evaporator. The crude solid was recrystallised from ethanol to yield a white crystalline solid (47.30 g, 66%, m.pt. 120° C.).

$^1$H NMR (DMSO) δ: 7.46 (6H, m), 6.95 (2H, m), 3.99 (2H, t), 1.80 (2H, quint), 1.38 (10H, m), 0.88 (3H, t). IR $\nu_{max}$/cm$^{-1}$: 2927, 2860, 1608, 1481, 1290, 1259, 844. MS m/z: 362 (M$^+$), 250, 221, 195, 182, 152, 139, 115, 89, 76, 69.

4-Octyloxybiphenyl-4'-yl boronic acid: A solution of n-butylithium (50.97 cm$^3$, 0.1274 mol, 2.5M in hexane) was added dropwise to a cooled (−78° C.) stirred solution of 4-bromo-4'-octyloxybiphenyl (40.00 g, 0.1108 mol) in THF (400 cm$^3$). After 1 h, trimethyl borate (23.05 g, 0.2216 mol) was added dropwise to the reaction mixture maintaining a temperature of −78° C. The reaction mixture was allowed to warm to room temperature overnight. 20% hydrochloric acid (350 cm$^3$) was added and the resultant mixture stirred for 1 h. The product was extracted into diethyl ether (3×300 cm$^3$). The combined organic layers were washed with water (300 cm$^3$), dried (MgSO$_4$), filtered and the filtrate evaporated down under partially reduced pressure. The crude product was stirred with hexane for 30 minutes and filtered off to yield a white powder (26.20 g, 73%, m.pt. 134-136° C.).

$^1$H NMR (DMSO) δ: 8.04 (2H, s), 7.84 (2H, m), 7.57 (4H, m), 7.00 (2H, m), 3.99 (2H, t), 1.74 (2H, quint), 1.35 (10H, m), 0.85 (3H, t). IR $\nu_{max}$/cm$^{-1}$: 2933, 2860, 1608, 1473, 1286, 1258, 818. MS m/z: 326 (M$^+$), 214, 196, 186, 170, 157, 128, 115, 77, 63

9,9-Diethyl-2,7-bis(4-octyloxybiphenyl-4'-yl)fluorene: Tetrakis(triphenylphosphine)palladium(0) (0.70 g, 0.0006 mol) was added to a stirred solution of 2,7-dibromo-9,9-diethylfluorene (4) (2.33 g, 0.0061 mol), 4-octyloxybiphenyl-4'-yl boronic acid (5.00 g, 0.0153 mol), 20% sodium carbonate solution (100 cm$^3$) and 1,2-dimethoxyethane (150 cm$^3$). The reaction mixture was heated under reflux overnight. Water (300 cm$^3$) was added to the cooled reaction mixture and the product extracted into DCM (3×300 cm$^3$). The combined organic extracts were washed with brine (2×150 cm$^3$), dried (MgSO$_4$)), filtered and the filtrate evaporated down under partially reduced pressure. The residue was purified by column chromatography on silica gel using DCM and hexane (30:70) as eluent and recrystallisation from ethanol and DCM to yield a white crystalline solid (3.10 g, 65%, m.pt. 146° C.).

$^1$H NMR (DMSO) δ: 7.77 (6H, m), 7.63 (12H, m), 7.00 (4H, m), 4.01 (4H, t), 2.13 (4H, quart), 1.82 (4H, quint), 1.40 (20H, m), 0.89 (6H, t), 0.43 (6H, t). IR $v_{max}$/cm$^{-1}$: 3024, 2921, 2853, 1609, 1501, 1463, 1251, 808. MS m/z: 782 (M$^+$), 669, 514, 485, 279, 145, 121, 107, 83, 71. CHN analysis: % Expected C (87.42%), H (8.49%). % Found C (87.66%), H (8.56%).

9,9-Diethyl-2,7-bis(4-hydroxybiphenyl-4'-yl)fluorene: Boron tribromide (99.9%, 1.05 cm$^3$, 0.0111 mol) in DCM (10 ml) was added dropwise to a cooled (0° C.) stirred solution of 9,9-diethyl-2,7-bis(4-octyloxybiphenyl-4'-yl)fluorene (2.90 g, 0.0037 mol) in DCM (100 cm$^3$). The reaction mixture was stirred at room temperature overnight, then poured onto an ice/water mixture (50 g) and stirred (30 minutes). The crude product was purified by column chromatography on silica gel with a mixture of ethyl acetate and hexane (30:70) as the eluent and recrystallisation from ethanol to yield a white powder (0.83 g, 40%, m.pt. >300° C.).

$^1$H NMR (DMSO) δ: 9.09 (2H, OH), 7.77 (6H, m), 7.64 (8H, m), 7.51 (4H, m), 6.94 (4H, m), 1.19 (4H, m), 0.42 (6H, t). IR $v_{max}$/cm$^{-1}$: 1608, 1500, 1463, 1244, 1173, 811. MS m/z: 558 (M$^+$), 529, 514, 313, 279, 257, 115, 77, 65.

Compound 8: 9,9-Diethyl-2,7-bis{4-[5-(1-vinylallyloxycarbonyl)pentyloxy]biphenyl-4'-yl}fluorene: Compound 8 was synthesised as follows:

A mixture of 9,9-diethyl-2,7-bis(4-hydroxybiphenyl-4'-yl)fluorene (0.83 g, 0.0015 mol), 1,4-pentadienyl-3-yl 6-bromohexanoate (0.97 g, 0.0037 mol), potassium carbonate (0.62 g, 0.0045 mol) and DMF (25 cm$^3$) was heated under reflux overnight. The cooled reaction mixture was added to water (500 cm$^3$) and then extracted with DCM (3×50 cm$^3$). The combined organic extracts were washed with water (250 cm$^3$), dried (MgSO$_4$) and the filtrate evaporated down under partially reduced pressure. The crude product was purified by column chromatography using silica gel using a mixture of DCM and hexane (80:20) as the eluent and recrystallisation from DCM and ethanol to yield a white crystalline solid (0.2 g, 22%).

$^1$H NMR (CDCl$_3$) δ: 7.78 (6H, m), 7.62 (12H, m), 7.00 (4H, m), 5.85 (4H, m), 5.74 (4H, m), 5.27 (4H, m), 4.03 (4H, t), 2.42 (4H, t), 2.14 (4H, quart), 1.85 (4H, m), 1.74 (4H, m), 1.25 (4H, q), 0.43 (3H, t). IR $v_{max}$/cm$^{-1}$: 3028, 2922, 2870, 1734, 1606, 1500, 1464, 1246, 1176, 812. CHN analysis: % Expected C (82.32%), H (7.24%). % Found C (81.59%), H (6.93%).

Compounds 9-15: Compounds 9 to 15, comprising the 2,7-bis{ω-[5-(1-vinylallyloxycarbonyl)alkoxy]-4'-biphenyl}-9,9-dialkylfluorenes compounds of Table 1 were prepared analogously to Compound 8.

| | n | m |
|---|---|---|
| Compound 9 | 3 | 5 |
| Compound 10 | 4 | 5 |
| Compound 11 | 5 | 5 |
| Compound 12 | 6 | 5 |
| Compound 13 | 8 | 5 |
| Compound 14 | 8 | 7 |
| Compound 15 | 8 | 11 |

All of Compounds 8 to 15 exhibit a nematic phase with a clearing point (N-I) between 58 and 143° C.

Compound 16: 4,7-bis{4-[(S)-3,7-Dimethyl-oct-6-enyloxy]phenyl}-2,1,3-benzothiadozole Compound 16 was synthesised as depicted in Reaction Scheme 8. Full details of each step follows:

4,7-Dibromo-2,1,3-benzothiadozole: Bromine (52.8 g, 0.33 mol) was added to a solution of 2,1,3-benzothiadozole (8.1 g, 0.032 mol) in hydrobromic acid (47%, 100 cm$^3$) and the resultant solution was heated under reflux for 2.5 h. The cooled reaction mixture reaction mixture was filtered and the solid product washed with water (200 cm$^3$) and sucked dry. The raw product was purified by recrystallisation from ethanol to yield 21.0 g (65%) of the desired product.

1-Bromo-4-[(S)-3,7-dimethyloct-6-enyloxy]benzene: A mixture of 4-bromophenol (34.6 g, 0.20 mol), (S)-(+)-citronellyl bromide (50 g, 0.023 mol) and potassium carbonate (45 g, 0.33 mol) in butanone (500 cm$^3$) was heated under reflux overnight. The cooled reaction mixture was filtered and the filtrate concentrated under reduced pressure. The crude product was purified by fractional distillation to yield 42.3 g (68.2%) of the desired product.

4-[(S)-3,7-Dimethyloct-6-enyloxy]phenyl boronic acid: 2.5M n-Butylithium in hexanes (49.3 cm$^3$, 0.12 mol) was added dropwise to a cooled (−78° C.) solution of 1-bromo-4-[(S)-3,7-dimethyloct-6-enyloxy]benzene (35 g, 0.11 mol) in tetrahydrofuran (350 cm$^3$). The resultant solution was stirred at this temperature for 1 h and then trimethyl borate (23.8 g, 0.23 mol) was added dropwise to the mixture while maintaining the temperature at −78° C. 20% hydrochloric acid (250 cm$^3$) was added and the resultant mixture was stirred for 1 h and then extracted into diethyl ether (2×200 cm$^3$). The combined organic layers were washed with water (2×100 cm$^3$) and dried (MgSO$_4$). After filtration the solvent was removed under reduce pressure to yield 20.35 g (65%) of the desired product.

4,7-bis{4-[(S)-3,7-Dimethyl-oct-6-enyloxy]phenyl}-2,1,3-benzothiadozole: A mixture of tetrakis(triphenylphosphine)palladium(0) (0.8 g, 0.70×10$^{-3}$ mol), 4,7-dibromo-2,1,3-benzothiadozole (2) (2 g, 6.75×10$^{-3}$ mol), 4-[(S)-3,7-dimethyloct-6-enyloxy]phenyl boronic acid (4.66 g, 1.70×10$^{-2}$ mol), 2M sodium carbonate solution (50 cm$^3$) and 1,2-dimethoxyethane (150 cm$^3$). The reaction mixture was heated under reflux overnight. The cooled reaction mixture was extracted with dichloromethane (2×150 cm³) and the combined organic layers were washed with brine (2×100 cm³) and dried (MgSO₄). After filtration the solvent was removed under reduced pressure and the residue was purified by column chromatography [silica gel, dichloromethane: hexane 1:4] followed by recrystallisation from ethanol to yield 3.2 g (79.5%) of the desired product.

4,7-bis(4-Hydroxyphenyl)-2,1,3-benzothiadozole: Boron tribromide (1.51 cm³, 1.61×10⁻² mol) was added dropwise to a cooled (0° C.) stirred solution of 2,5-bis{4-[(S)-3,7-dimethyl-oct-6-enyloxy]phenyl}-2,1,3-benzothiadozole (4.0 g, 7.40×10⁻³ mol) in dichloromethane (100 cm³). The reaction mixture was stirred at room temperature overnight, then poured onto an ice/water mixture (200 g) and stirred (30 min). The desired product was precipitated and it was filtered off and sucked dry to yield 1.23 g (71.5%) of the desired product.

4,7-bis(4-{5-[1-Vinyl-allyloxycarbonyl]pentyloxy}phenyl)-2,1,3-benzothiadozole: A mixture of 2,5-bis(4-hydroxyphenyl)-2,1,3-benzothiadozole (0.3 g, 0.93×10⁻³ mol), 1,4-pentadien-3-yl 5-bromopentanoate (0.61 g, 2.34×10³¹ mol) and potassium carbonate (0.38 g, 2.79×10⁻³ mol) in N,N-dimethylformaldehyde (30 cm³) was heated (80 C°) overnight. The cooled reaction mixture was filtered and the filtrate concentrated under reduce pressure. The crude product was purified by column chromatography [silica gel, ethyl acetate:hexane 1:5] followed by recrystallisation from ethanol to yield 0.39 g (61.8%) of the desired product.

Compounds 17 and 18 are preparable by an analogous process.

Thin Film Polymerisation and Evaluation

Thin films of Compounds 3 to 6 and Compounds 9 to 15 were prepared by spin casting from a 0.5%-2% M solution in chloroform onto quartz substrates. All sample processing was carried out in a dry nitrogen filled glove box to avoid oxygen and water contamination. The samples were subsequently baked at 50° C. for 30 minutes, heated to 90° C. and then cooled at a rate of 0.2° C. to room temperature to form a nematic glass. Polarised microscopy showed that no change was observed in the films over several months at room temperature. The films were polymerized in a nitrogen filled chamber using light from an Argon Ion laser. Most of the polymerization studies were carried out at 300 nm with a constant intensity of 100 MWcm⁻² and the total fluence varied according to the exposure time. No photoinitiator was used. Temperature dependent polymerization studies were carried out in a Linkham model LTS 350 hot-stage driven by a TP 93 controller under flowing nitrogen gas. A solubility test was used to find the optimum fluence: different regions of the film were exposed to UV irradiation with different fluences and the film was subsequently washed in chloroform for 30 s. The unpolymerized and partially polymerized regions of the film were washed away and PL from the remaining regions was observed on excitation with an expanded beam from the Argon Ion laser. Optical absorbance measurements were made using a Unicam 5625 UV-VIS spectrophotometer. PL and EL were measured in a chamber filled with dry nitrogen gas using a photodiode array (Ocean Optics S2000) with a spectral range from 200 nm to 850 nm and a resolution of 2 nm. Films were deposited onto CaF₂ substrates for Fourier Transform infrared measurements, which were carried out on a Perkin Elmer Paragon 1000 Spectrometer. Indium tin oxide (ITO) coated glass substrates, (Merck 15 Ω/□) were used for EL devices. These were cleaned using an Argon plasma. ²⁰ A PDOT (EL-grade, Bayer) layer of thickness 45 nm±10% was spin-cast onto the substrate and baked at 165° C. for 30 minutes. This formed a hole-transporting film. One or more organic films of thickness≈45 nm were subsequently deposited by spin-casting and crosslinked as discussed below. Film thicknesses were measured using a Dektak surface profiler. Aluminum was selectively evaporated onto the films at a pressure less than 1×10⁻⁵ torr using a shadow mask to form the cathode.

Photopolymerisation Details

The optimum fluences required in order to polymerize the diene monomers (Compounds 3 to 6) efficiently with a minimum of photodegradation, were found to be 100 Jcm⁻², 20 Jcm⁻², 100 Jcm⁻² and 300 Jcm⁻² respectively, using the solubility test. As Scheme 6 shows, the 1,6-heptadiene monomer (e.g. Compound 4) forms a network with a repeat unit containing a single ring. Its polymerization rate is equal to that of the 1,4-pentadiene monomer (e.g. Compounds 3 and 5) but the increase of PL intensity after polymerization is less for Compound 4. This may be because of the increased flexibility of the C₇ ring in the backbone of the crosslinked material. The 1,4-pentadiene diene monomers (Compounds 3 and 5) are homologues and differ only in the length of the flexible alkoxy-spacer part of the end-groups. The PL spectrum of Compound 5 with the shorter spacer is significantly different to all other materials before exposure suggesting a different conformation. The higher fluence required to polymerize the 1,4-pentadiene monomer Compound 5 implies that the polymerization rate is dependent on the spacer length: the freedom of motion of the photopolymerizable end-group is reduced, because of the shorter aliphatic spacer in Compound 5. The diallylamine monomer Compound 6 has a significantly different structure to the dienes. It is much more photosensitive than the other diene monomers because of the activation by the electron rich nitrogen atom. Scheme 6 also shows (by way of comparison) that when a methacrylate monomer is employed the polymerization step does not involve the formation of a ring.

Photopolymerization Characteristics

The absorbance and PL spectra of 1,4-pentadiene monomer (Compound 3) were measured before and after exposure with the optimum UV fluence of 100 J cm⁻². The latter measurements were repeated after washing in chloroform for 30 s. The absorbance spectra of the unexposed and exposed films are almost identical and the total absorbance decreases by 15% after washing indicating that only a small amount of the material is removed. This confirms conclusively that a predominantly insoluble network is formed.

The UV irradiation was carried out in the nematic glass phases at room temperature at 300 nm. The excitation of the fluorene chromophore is minimal at this wavelength and the absorbance is extremely low. The experiment was repeated using a wavelength of 350 nm near the absorbance peak. Although the number of absorbed photons is far greater at 350 nm, a similar fluence is required to form an insoluble network. Furthermore excitation at 350 nm results in some photodegradation. UV photopolymerization was also carried out at 300 nm at temperatures of 50° C., 65° C. and 80° C. all in the nematic phase. It was anticipated that the polymerization rate would increase, when the photoreactive mesogens were irradiated in the more mobile nematic phase. However, the fluence required to form the crosslinked network was independent of temperature, within the resolution of our solubility test. Furthermore, the integrated PL intensity from the crosslinked network decreases with temperature indicating a temperature dependent photodegradation.

Bilayer Electroluminescent Devices

Bilayer electroluminescent devices were prepared by spin-casting the 1,4-pentadiene monomer (Compound 3) onto a hole-transporting PEDT layer. The diene functioned as the light-emitting and electron-transporting material in the stable nematic glassy state. Equivalent devices using cross-linked networks formed from Compound 3 by photopolymerisation with UV were also fabricated on the same substrate under identical conditions and the EL properties of both types of devices evaluated and compared. The fabrication of such bilayer OLEDs is facilitated by the fact that the hole-transporting PEDT layer is insoluble in the organic solvent used to deposit the electroluminescent and electron-transporting reactive mesogen (Compound 3). Half of the layer of Compound 3 was photopolymerized using optimum conditions and the other half was left unexposed so that EL devices incorporating either the nematic glass or the cross-linked polymer network could be directly compared on the same substrate under identical conditions. Aluminum cathodes were deposited onto both the cross-linked and non cross-linked regions. Polarized electroluminescent devices were prepared by the polymerization of uniformly aligned Compound 3 achieved by depositing it onto a photoalignment layer doped with a hole transporting molecule. In these devices external quantum efficiencies of 1.4% were obtained for electroluminescence at 80 cd m$^{-2}$. Three layer devices were also prepared by spin-casting an electron transporting polymer (Compound 7), which shows a broad featureless blue emission, on top of the crosslinked nematic polymer network. In the case of both the three layer and bilayer devices the luminescence originates from the cross-linked polymer network of the 1,4-pentadiene monomer (Compound 3). The increased brightness of the three-layer device may result from an improved balance of electron and hole injection and/or from a shift of the recombination region away from the absorbing cathode.

Multilayer Device

Figure 2:
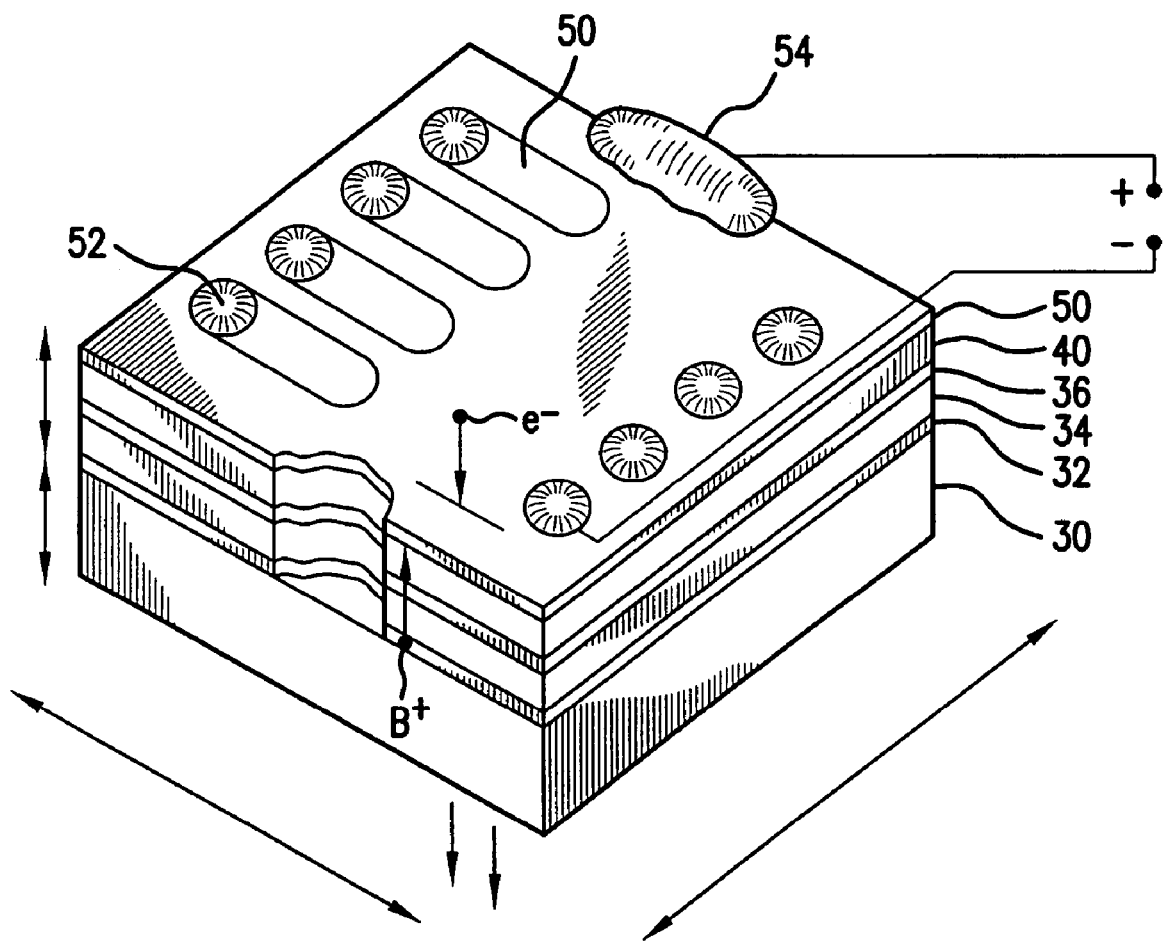
FIG. 2 is a representation of a display device in accord with the present invention.

A multilayer device configuration was implemented as illustrated in FIG. 2. A glass substrate 30 (12 mm×12 mm×1 mm) coated with a layer of indium tin oxide 32 (ITO) was cleaned via oxygen plasma etching. Scanning electron microscopy revealed an improvement in the surface smoothness by using this process which also results in a beneficial lowering of the ITO work function. The ITO was coated with two strips (~2 mm) of polyimide 34 along opposite edges of the substrate then covered with a polyethylene dioxthiophene/polystyrene sulfonate (PEDT/PSS) EL-grade layer 36 of thickness 45±5 nm deposited by spin-coating. The layer 36 was baked at 165° C. for 30 min in order to cure the PEDT/PSS and remove any volatile contaminants. The doped polymer blend of Compounds 1 and 2 was spun from a 0.5% solution in cyclopentanone forming an alignment layer 40 of thickness ~20 nm. This formed the hole-injecting aligning interface after exposure to linearly polarized CV from an argon ion laser tuned to 300 nm. A liquid-crystalline luminescent layer 50 of Compound 3 was then spun cast from a chloroform solution forming a film of ~10 nm thickness. A further bake at 50° C. for 30 min was employed to drive off any residual solvent. The sample was heated to 100° C. and slowly cooled at 02° C./min to room temperature to achieve macroscopic alignment of chromophores in the nematic glass phase. Irradiation with UV light at 300 nm from an argon ion laser was used to induce crosslinking of the photoactive end-groups of the Compound 3 to form an insoluble and intractable layer. No photoinitiator was used hence minimizing continued photoreaction during the device lifetime. Aluminium electrodes 50 were vapor-deposited under a vacuum of 10° mbar or better and silver paste dots 52 applied for electrical contact. A silver paste contact 54 was also applied for contact with the indium tin oxide base electrode. This entire fabrication process was carried out under dry nitrogen of purity greater than 99.99%. Film thickness was measured using a Dektak ST surface profiler.

The samples were mounted for testing within a nitrogen-filled chamber with spring-loaded probes. The polymide strips form a protective layer preventing the spring-loaded test probes from pushing through the various layers. Optical absorbance measurements were taken using a Unicam UV-vis spectrometer with a polarizer (Ealing Polarcaot 105 UV-vis code 23-2363) in the beam. The spectrometer's polarization bias was taken into account and dichroic ratios were obtained by comparing maxima at around 370-380 nm.

Luminescence/voltage measurements were taken using a photomultiplier tube (EMI 6097B with S11 type photocathode) and Keithley 196 multimeter with computer control. Polarized EL measurements were taken using a photodiode array (Ocean Optics S2000, 200-850 nm bandwidth 2 nm resolution) and polarizer as described above. The polarization bias of the spectrometer was eliminated by use of an input fiber (fused silica 100 μm diameter) ensuring complete depolarisation of light into the instrument.

Monochrome Backlight

Figure 3:
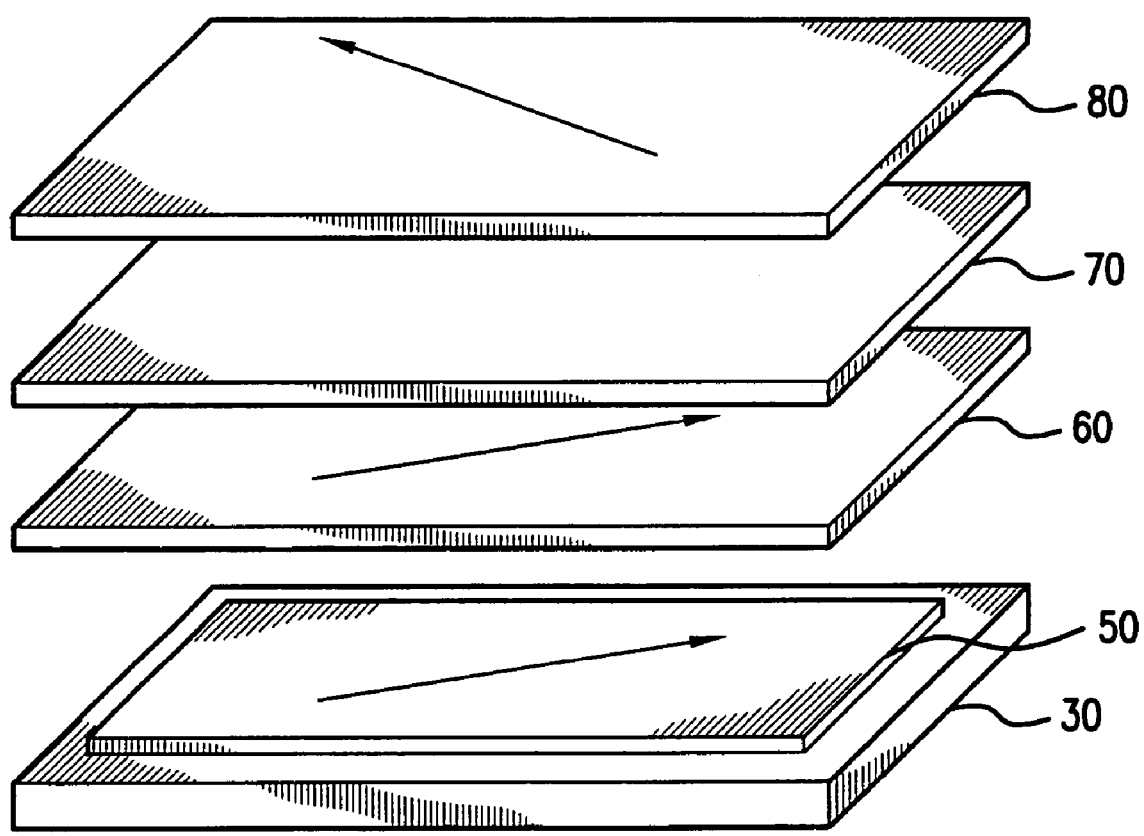
FIG. 3 is a representation of a backlight in accord with the present invention.
Figure 4:
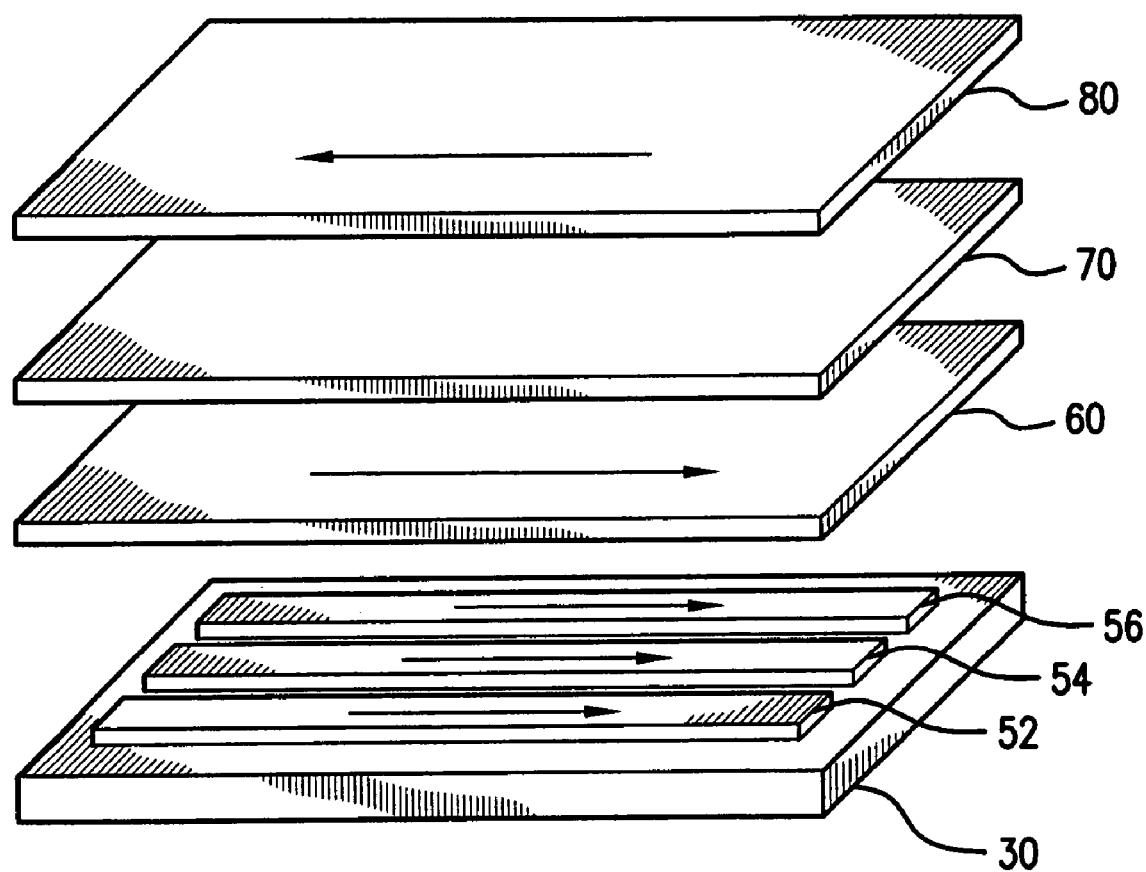
FIG. 4 is a representation of a polarised sequential light emitting backlight in accord with the present invention.
Figure 5:
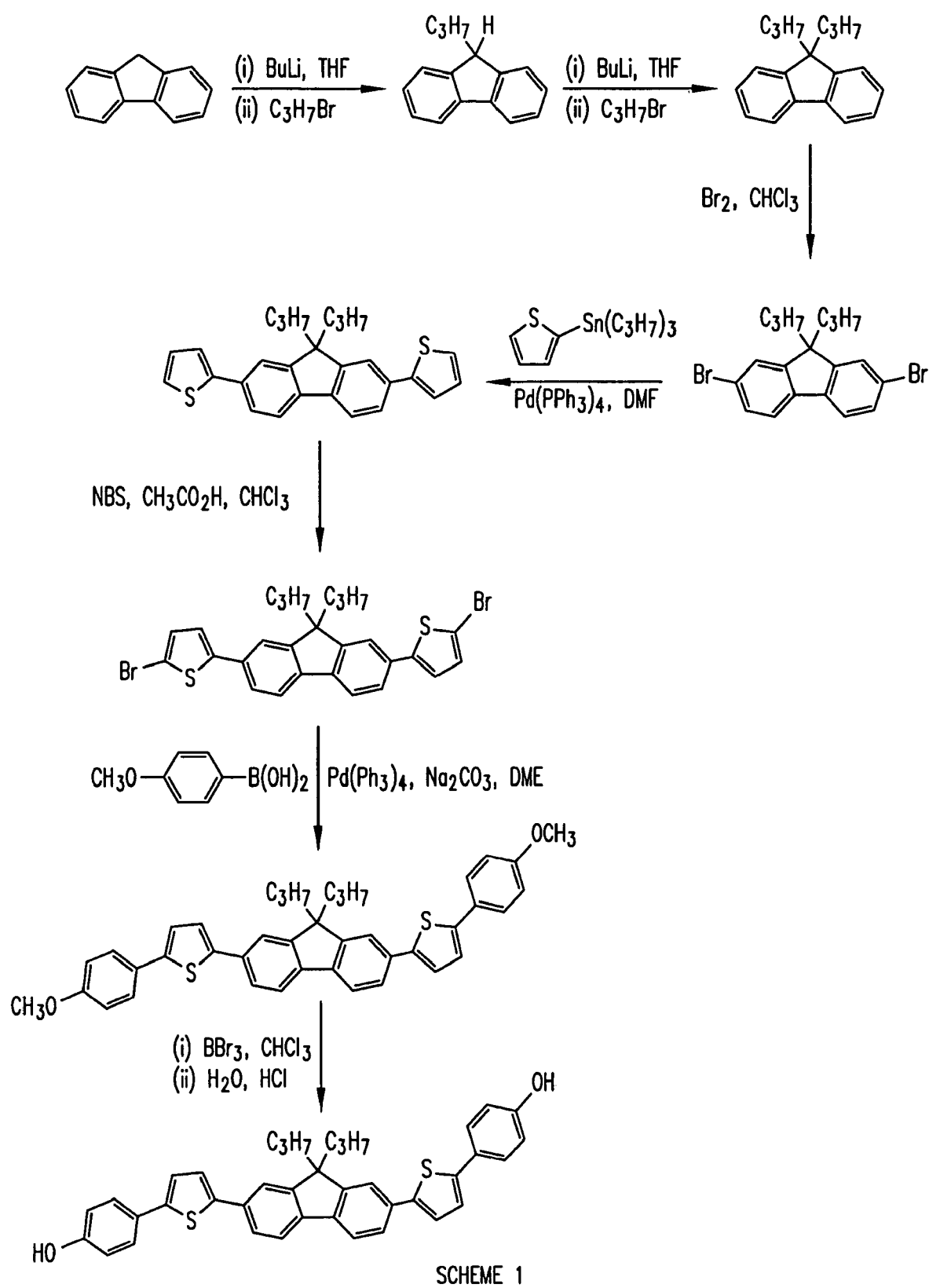
FIGS. 5 to 12 show reaction schemes 1 to 8, respectively.
Figure 6:
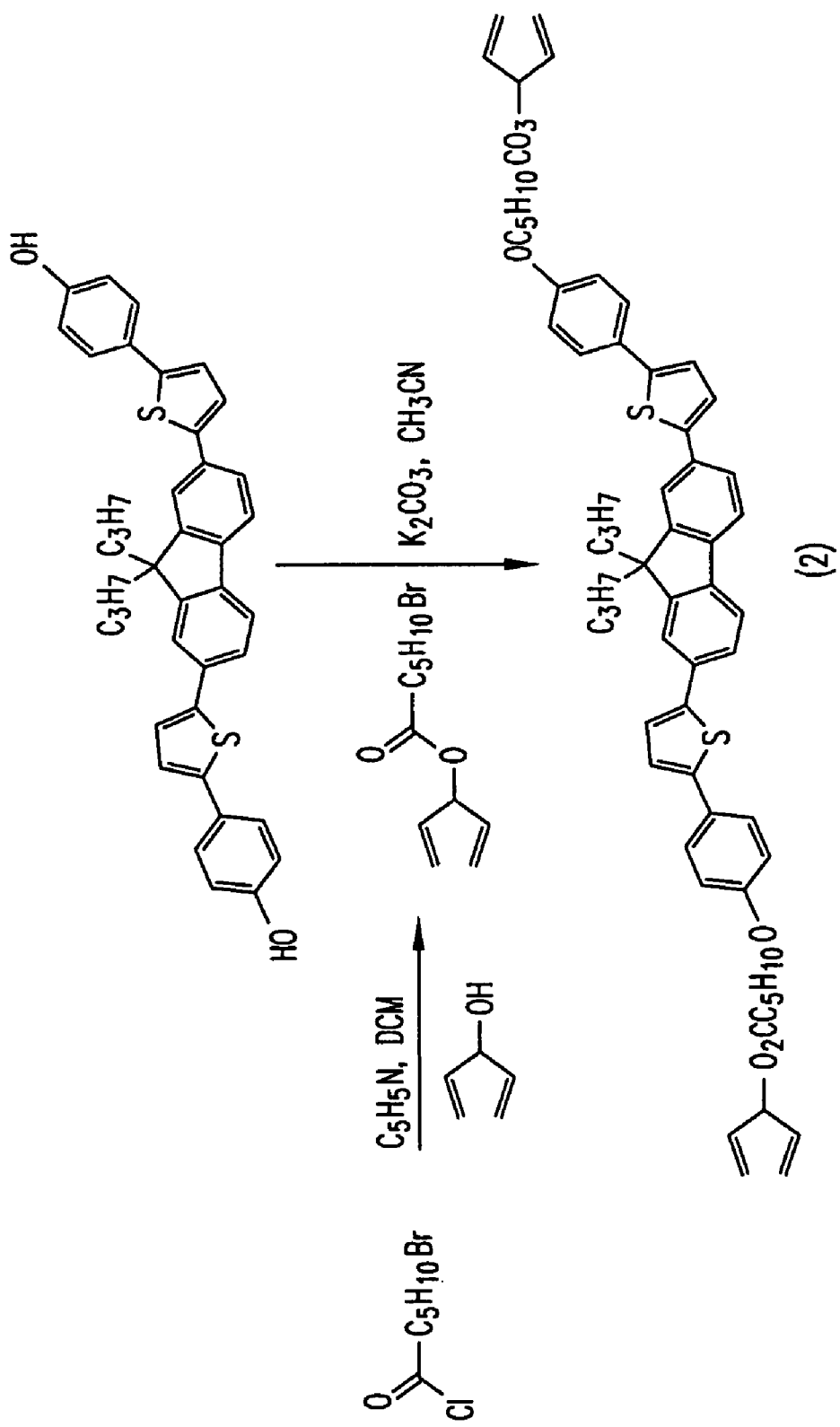
Figure 7:
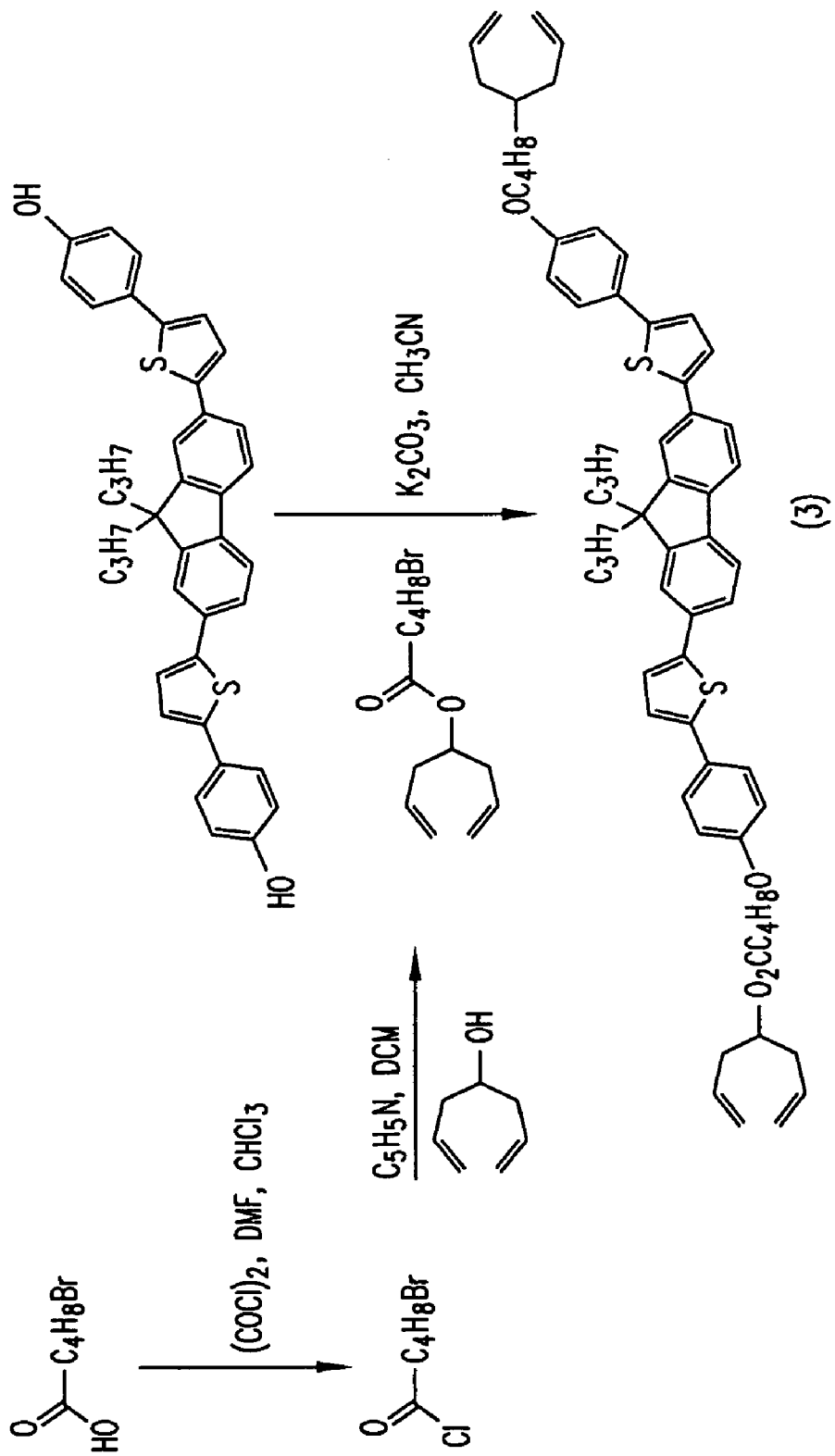

FIG. 3 shows a schematic representation of a polarised light monochrome backlight used to illuminate a twisted nematic liquid crystal display. The arrows indicate the polarisation direction. An inert substrate 30 (e.g. glass coated with a layer of indium tin oxide (ITO) as in FIG. 2) is provided with a layer 50 of a polarised light emitting polymer (e.g. comprising Compound 3 as in FIG. 2). The assembly further includes a clean up polariser 60 comprising a high transmission low polarisation efficiency polariser; a twisted nematic liquid crystal display 70; and a front polariser 80. It will be appreciated that the light emitting polymer layer 50 acts as a light source for the liquid crystal display 70.

Polarised Light Sequential Tricolor Backlight

FIG. 3 schematic of a polarised light sequential red, green and blue light emitting backlight used to illuminate a fast liquid crystal display (ferroelectric display). The arrows indicate the polarisation direction. An inert substrate 30 (e.g. glass coated with a layer of indium tin oxide (ITO) as in FIG. 2) is respectively provided with red 52, green 54 and blue 56 striped layers of a polarised light emitting polymer (e.g. comprising Compound 3 as in FIG. 2 and a suitable dye molecule as a dopant). The assembly further includes a clean up polariser 60 comprising a high transmission low polarisation efficiency polariser; a fast (ferroelectric) liquid crystal display 70; and a front polariser 80. It will be appreciated that the striped light emitting polymer layer 52, 54, 56 acts as a light source for the fast liquid crystal display 70. The sequential emission of the RGB stripes corresponds with the appropriate colour image on the fast liquid crystal display. Thus, a colour display is seen.

Alignment Characteristics

The PL polarization ratio ($PL_\eta/PL_\perp$) of the aligned polymer formed from Compound 3 in its nematic glass phase can be taken as a measure of the alignment quality. Optimum alignment is obtained with the undoped alignment layer for an incident fluence of 50 mJ cm$^{-2}$. The alignment quality deteriorates when higher fluences are used. This is expected because there are competing LC-surface interactions giving parallel and perpendicular alignment respectively. When the dopant concentration is 40% or higher there is a detrimental effect on alignment. However with concentrations up to 30% the polarization ratio of emitted light is not severely effected although higher fluences are required to obtain optimum alignment. The EL intensity reaches its peak for the ~50% mixture. A 30% mixture offers a good compromise in balancing the output luminescence intensity and polarization ratio. From these conditions and using the 30% doped layer we have observed strong optical dichroism in the absorbance (D~6.5) and obtained PL polarization ratios of 8:1.

Electroluminescence Characteristics

Devices made with compound 3 in the nematic glassy state showed poor EL polarization ratios because the low glass transition temperature compromised the alignment stability. Much better performance was achieved when compound 3 was crosslinked.

A brightness of 60 cd m$^{-2}$ (measured without polarizer) was obtained at a drive voltage of 11V. The threshold voltage, EL polarization ratio and intensity all depend on the composition of the alignment layer. A luminance of 90 cd m$^{-2}$ was obtained from a 50% doped device but with a reduction in the EL polarization ratio. Conversely a polarized EL ratio of 11:1 is found from a 20% doped device but with lower brightness. A threshold voltage of 2V is found for the device with a hole-transporting layer with 100% of the dopant comprising compound 2. Clearly a photo-alignment polymer optimised for both alignment and hole-transporting properties would improve device performance. This could be achieved using a co-polymer incorporating both linear rod-like hole-transporting and photoactive side chains.

The invention claimed is:

1. A polymerizable reactive mesogen for forming a charge transporting or light emitting polymer comprising a reactive mesogen having the formula:

ti B-S-A-S-B wherein
   A is a chromophore;
   S is a spacer; and
   B is an endgroup which susceptible to photopolymerization,
wherein the photopolymerization involves cyclopolymerization.

2. The mesogen of claim 1, wherein the chromophore A is selected from the group consisting of fluorene, vinylenephenylene, anthracene, perylene and any derivatives thereof.

3. The mesogen of claim 1, wherein the spacer S is an organic chain.

4. The mesogen of claim 3, wherein the organic chain is selected from the group consisting of aliphatic, amine, ester and ether linkages and any derivatives thereof.

5. A polymerizable reactive mesogen for forming a charge transporting or light emitting polymer comprising a reactive mesogen having the formula:

B-S-A-S-B wherein
   A is a chromophore;
   S is a spacer; and
   B is an endgroup which is susceptible to photopolymerization and selected from the group consisting of 1,4 dienes, 1,5 dienes, 1,6 dienes and dienes wherein the diene functionalities are separated by an aliphatic linkage or by an inert linkage selected from the group consisting of ether an amine linkages.

6. The mesogen of claim 5, wherein the chromophore A is selected from the group consisting of fluorene, vinylenephenylene, anthracene, perylene and any derivatives thereof.

7. The mesogen of claim 6, wherein the spacer S is an organic chain.

8. The mesogen of claim 7, wherein the organic chain is selected from the group consisting of aliphatic, amine, ester and ether linkages and any derivatives thereof.

9. A polymerizable reactive mesogen for forming a charge transporting or light emitting polymer comprising a reactive mesogen having the formula:

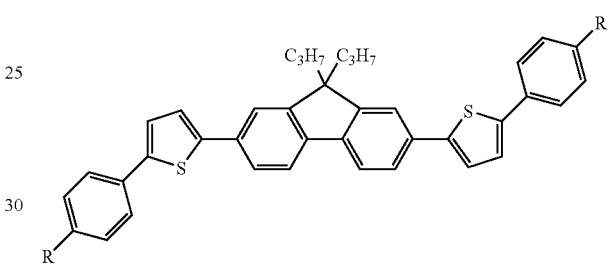

wherein R has the general formula: X—S2-Y-Z where
   X is selected from the group consisting of O, CH$_2$ and NH;
   S2 is selected from the group consisting of linear alkyl, branched alkyl and alkenyl chains optionally including a heteroatom;
   Y is selected from the group consisting of O, CO$_2$ and S; and
   Z is a diene.

10. The mesogen of claim 9, wherein
   X is O;
   S2 is a linear alkyl chain;
   Y is CO$_2$; and
   Z is selected from the group consisting of 1,4, 1,5 and 1,6 dienes.

11. A polymerizable reactive mesogen for forming a charge transporting or light emitting polymer comprising a reactive mesogen having the formula:

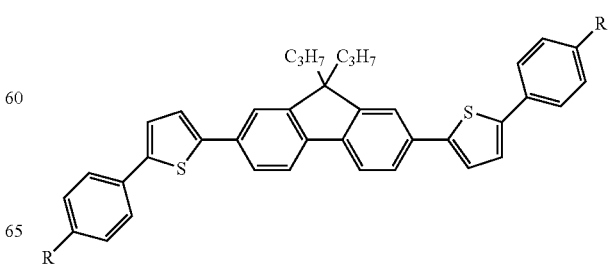

wherein R is selected from the group consisting of

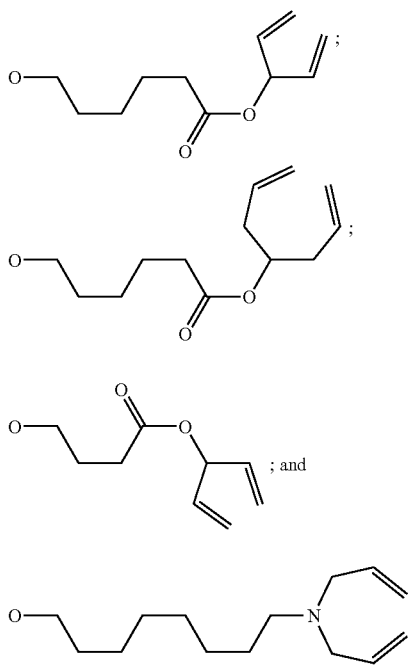

and any mixtures thereof.

12. A polymerizable reactive mesogen for forming a charge transporting or light emitting polymer comprising a reactive mesogen having the formula:

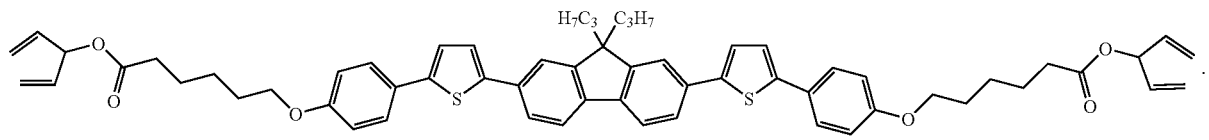

13. A polymerizable reactive mesogen for forming a charge transporting or light emitting polymer comprising a reactive mesogen having the formula:

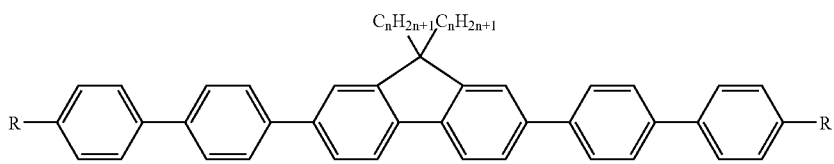

wherein n is from 2 to 10 and R has the general formula: X—S2-Y-Z, where
- X is selected from the group consisting of O, $CH_2$ and NH;
- S2 is selected from the group consisting of linear alkyl, branched alkyl and alkenyl chains optionally including a heteroatom;
- Y is selected from the group consisting of O, $CO_2$ and S; and
- Z is a diene.

14. The mesogen of claim 13, wherein
- X is O;
- S2 is a linear alkyl chain;
- Y is $CO_2$; and
- Z is selected from the group consisting of 1,4, 1,5 and 1,6 dienes.

15. The mesogen of claim 14, wherein R is selected from the group consisting of

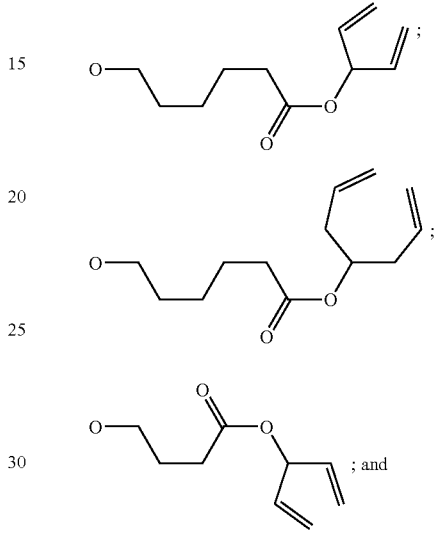

-continued

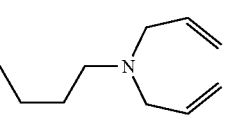

and any mixtures thereof.

16. The mesogen of claim 15, wherein the reactive mesogen has the formula:

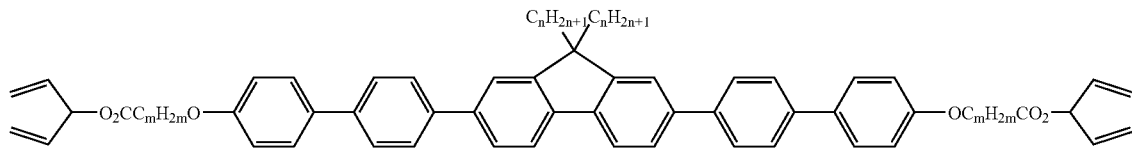

wherein:
n is from 2 to 10; and
m is from 4 to 12.

17. The mesogen of claim 16, wherein
$2 \leq n \leq 6$ and m=5, or
n=8 and m=5, 7 or 11.

18. A polymerizable reactive mesogen for forming a charge transporting or light emitting polymer comprising a reactive mesogen having the formula:

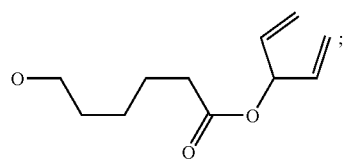

wherein A=H or F;
R has the general formula: X—S2-Y-Z;
X is selected from the group consisting of O, $CH_2$ and NH;
S2 is selected from the group consisting of linear alkyl, branched alkyl and alkenyl chains optionally including a heteroatom;
Y is selected from the group consisting of O, $CO_2$ and S; and
Z is a diene.

19. The mesogen of claim 18, wherein
X is O;
S2 is a linear alkyl chain; Y is $CO_2$; and
Z is selected from the group consisting of 1,4, 1,5 and 1,6 dienes.

20. The mesogen of claim 19, wherein R is selected from the group consisting of

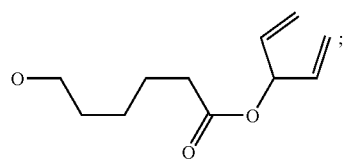

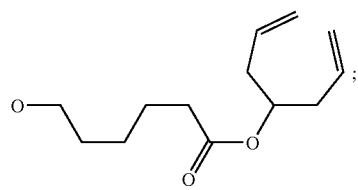

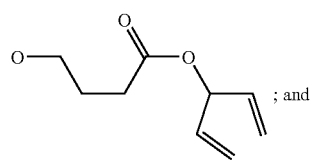

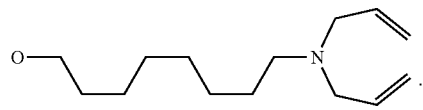

21. The mesogen of claim 18, wherein the reactive has the formula:

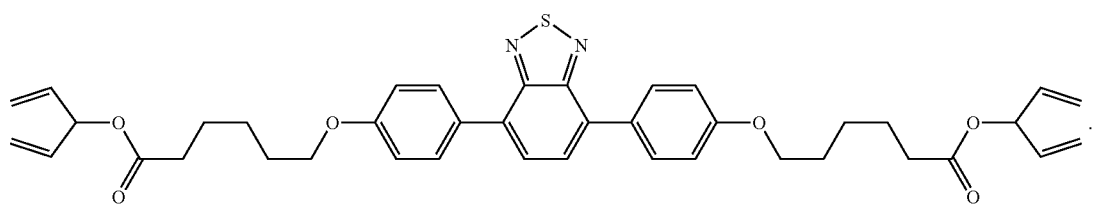

22. The mesogen of claim 18, wherein the reactive mesogen has the formula:

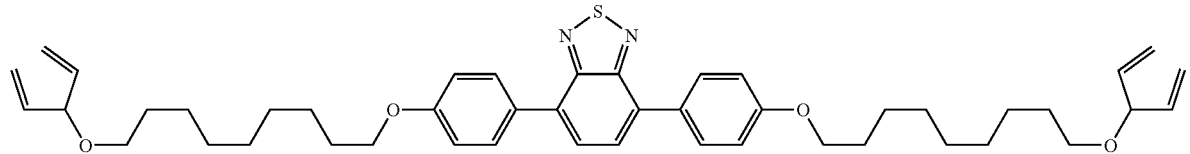

23. The mesogen of claim 18, wherein the reactive mesogen has the formula:

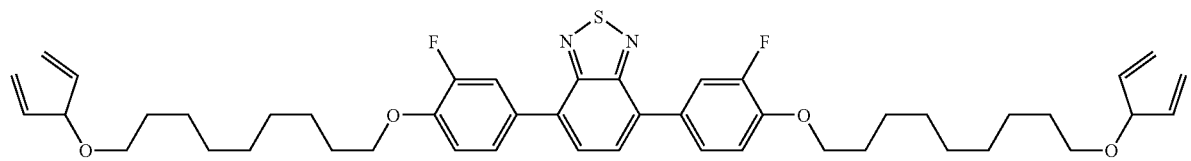

24. A backlight or display comprising a backlight or display including a polymerizable reactive mesogen for forming a charge transporting or light emitting polymer comprising the reactive mesogen of claim 1.

25. A backlight or display comprising a backlight or display including a polymerizable reactive mesogen for forming a charge transporting or light emitting polymer comprising the reactive mesogen of claim 5.

26. A backlight or display comprising a backlight or display including a polymerizable reactive mesogen for forming a charge transporting or light emitting polymer comprising the reactive mesogen of claim 9.

27. A backlight or display comprising a backlight or display including a polymerizable reactive mesogen for forming a charge transporting or light emitting polymer comprising the reactive mesogen of claim 11.

28. A backlight or display comprising a backlight or display including a polymerizable reactive mesogen for forming a charge transporting or light emitting polymer comprising the reactive mesogen of claim 12.

29. A backlight or display comprising a backlight or display including a polymerizable reactive mesogen for forming a charge transporting or light emitting polymer comprising the reactive mesogen of claim 13.

30. A backlight or display comprising a backlight or display including a polymerizable reactive mesogen for forming a charge transporting or light emitting polymer comprising the reactive mesogen of claim 18.

* * * * *

UNITED STATES PATENT AND TRADEMARK OFFICE
CERTIFICATE OF CORRECTION

PATENT NO. : 7,265,163 B2
APPLICATION NO. : 10/859446
DATED : September 4, 2007
INVENTOR(S) : Mary O'Neill et al.

Figure 8:
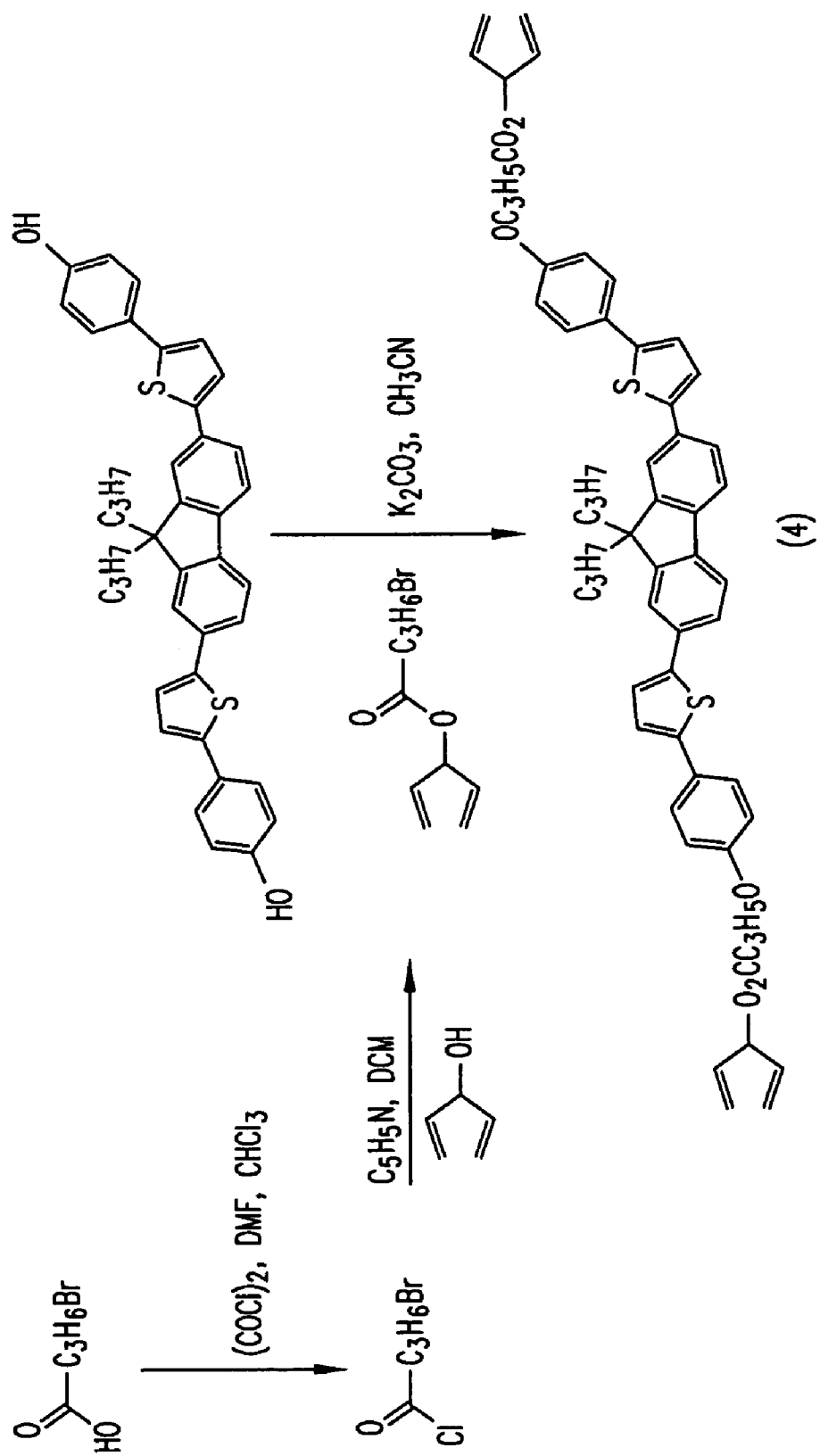

It is certified that error appears in the above-identified patent and that said Letters Patent is hereby corrected as shown below:

In FIG. 8

Please delete the formula "OC3H5CO2" and insert the formula -- OC3H6CO2 --.

Figure 9:
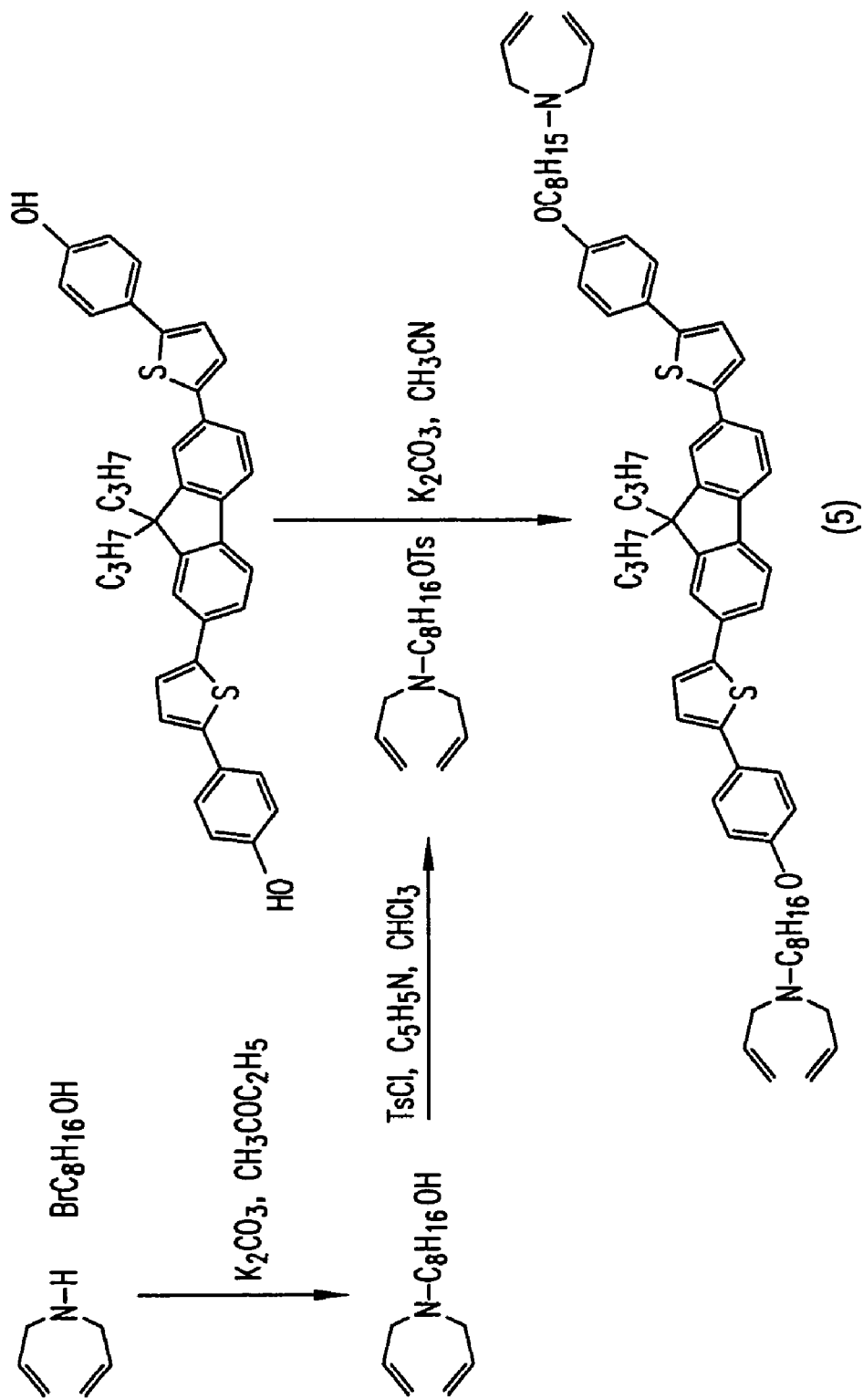
Figure 10:
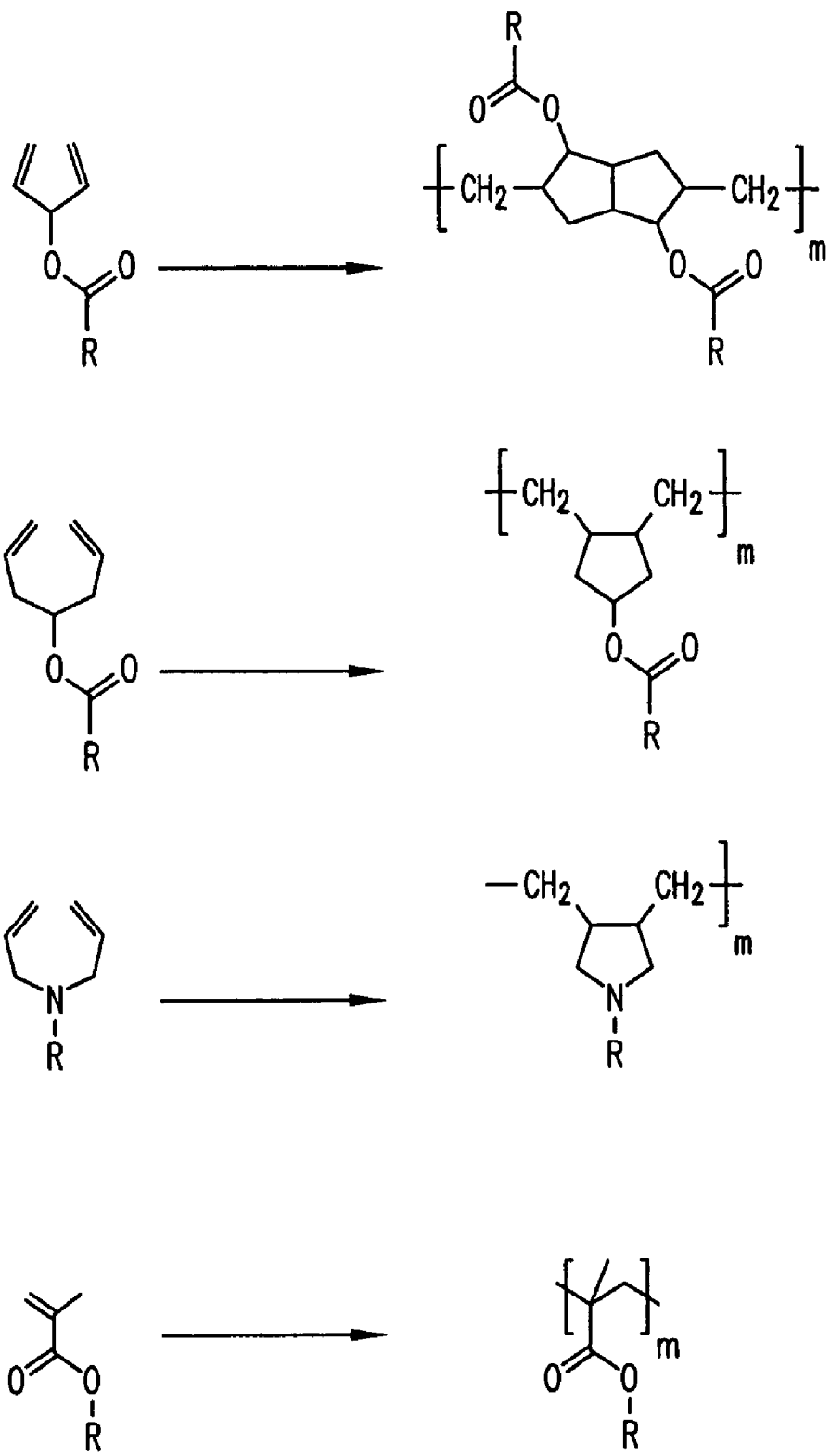
Figure 11:
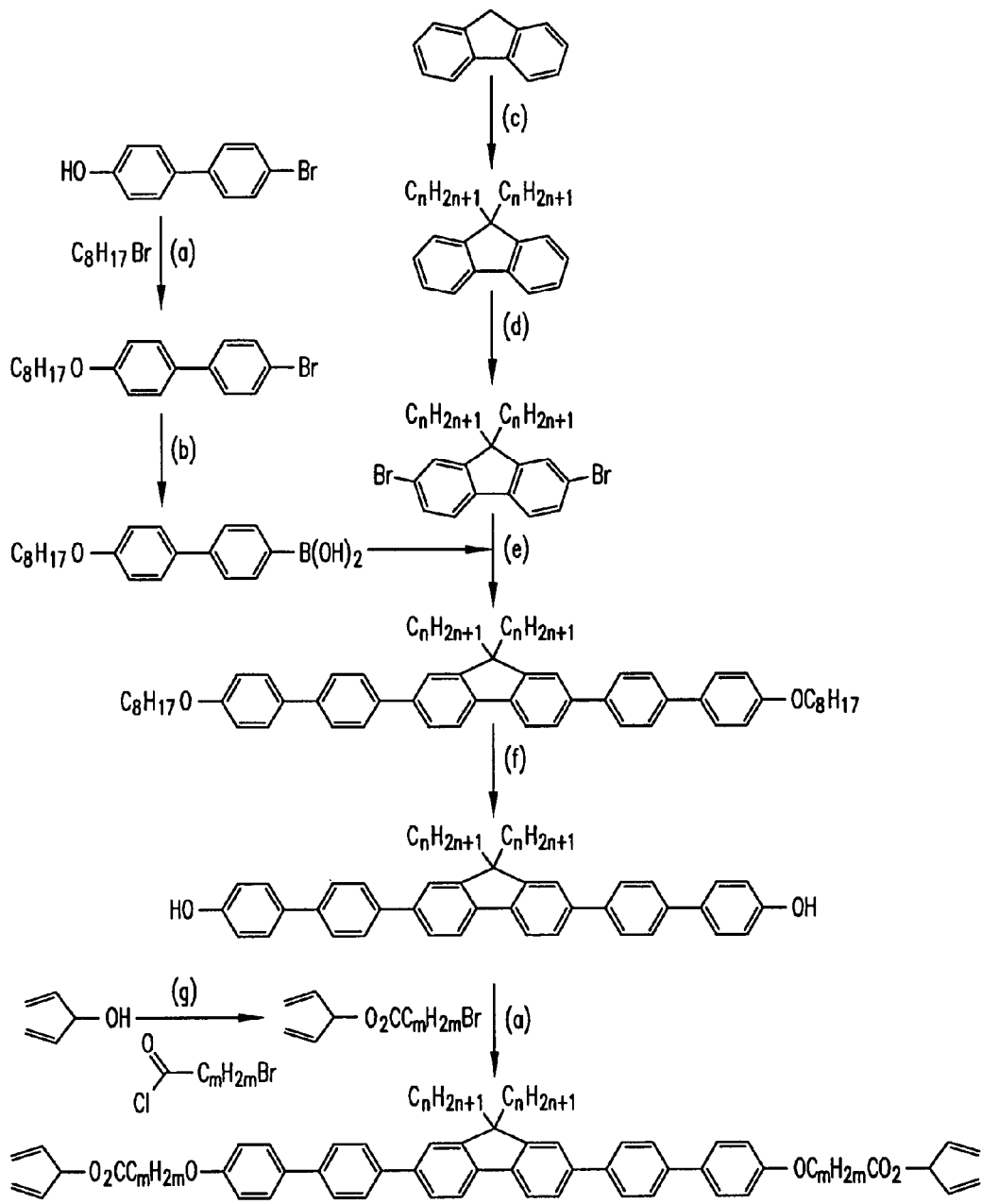

In FIG. 9

Please delete the formula "OC8H15-N" and insert the formula -- OC8H16-N --.

Figure 12:
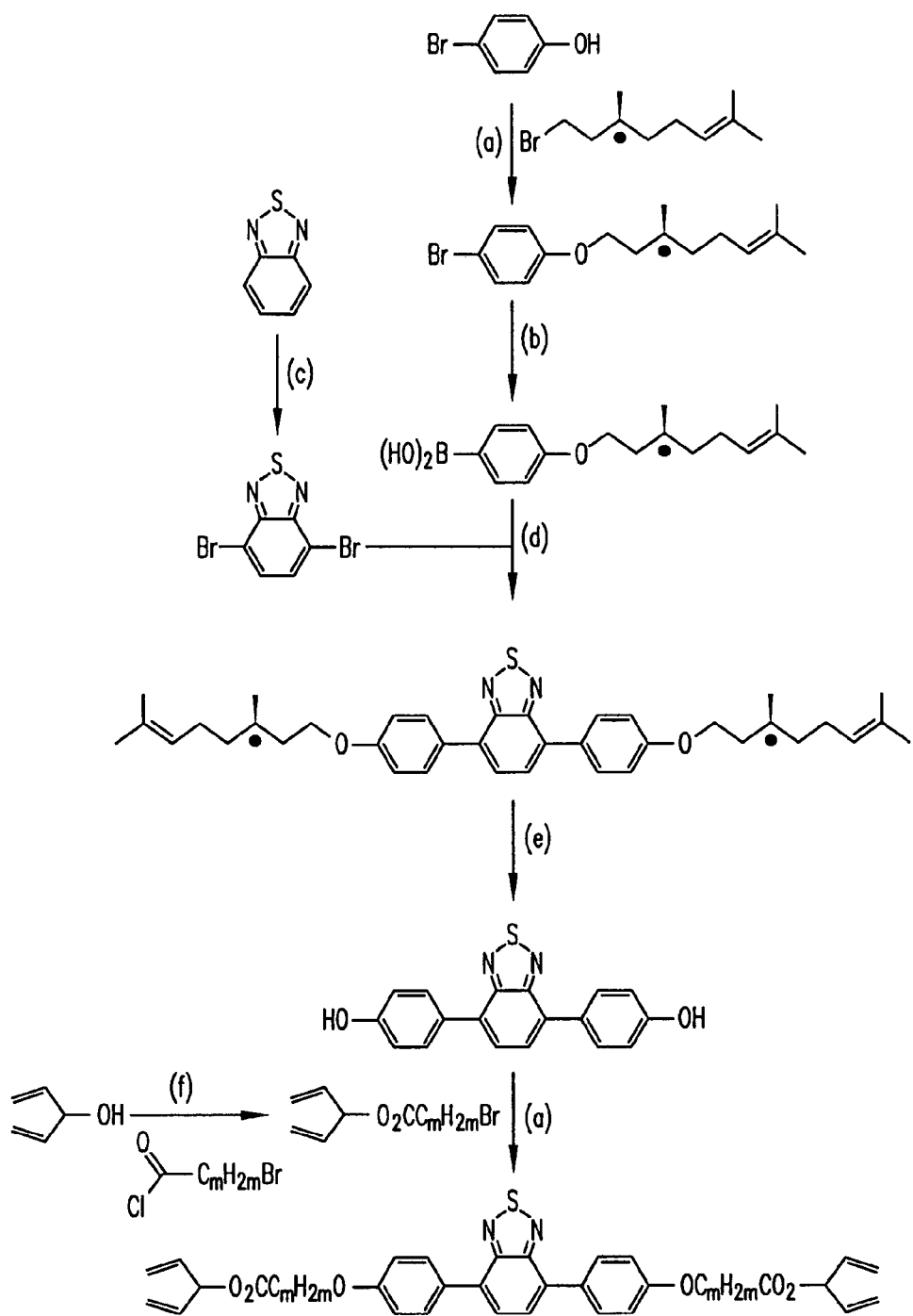

In FIG. 12

Please delete all "•" and insert -- * --.

In Column 7, Line 41

Please delete italicized brackets and replace with regular text brackets.

In Column 7, Line 42

Please delete the regular text term "tris" and replace with the italicized text.

In Column 7, Line 42

Please delete the regular text term "N" and replace with the italicized text.

UNITED STATES PATENT AND TRADEMARK OFFICE
CERTIFICATE OF CORRECTION

PATENT NO. : 7,265,163 B2
APPLICATION NO. : 10/859446
DATED : September 4, 2007
INVENTOR(S) : Mary O'Neill et al.

It is certified that error appears in the above-identified patent and that said Letters Patent is hereby corrected as shown below:

In Column 8, Line 45

Please delete the italicized brackets and replace with regular text brackets.

Signed and Sealed this

Twenty-third Day of December, 2008

JON W. DUDAS
*Director of the United States Patent and Trademark Office*